United States Patent [19]
Hirschberg et al.

[11] Patent Number: 5,792,903
[45] Date of Patent: Aug. 11, 1998

[54] LYCOPENE CYCLASE GENE

[75] Inventors: Joseph Hirschberg, Jerusalem, Israel; Francis Xavier Cunningham, Jr., Chevy Chase; Elisabeth Gantt, Bethseda, both of Md.

[73] Assignees: Yissum Research Development Company of Hebrew University of Jerusalem, Jerusalem 91042, Israel; University of Maryland, College Park, Md.

[21] Appl. No.: 399,561

[22] Filed: Mar. 7, 1995

Related U.S. Application Data

[63] Continuation-in-part of Ser. No. 142,195, Oct. 25, 1993, abandoned.

[51] Int. Cl.$^6$ .............................. A01H 5/00; C12N 1/00; C12N 5/04; C12N 15/29
[52] U.S. Cl. ...................... 800/200; 435/69.1; 435/70.1; 435/172.3; 435/320.1; 435/243; 435/252.3; 435/252.8; 435/419; 536/23.7
[58] Field of Search .............................. 435/69.1, 70.1, 435/172.3, 320.6, 240.1, 243, 252.3, 252.8, 419; 536/23.7; 800/200

[56] References Cited

PUBLICATIONS

Koyama, 1991, "Structures & functions of carotenoids in photosynthetic systems", *J. Photochem. Photobiol. B:Biol.* 9:265–280.

Siefermann–Harms, 1987, "The Light–harvesting and protective functions of carotenoids in photosynthetic membranes", *Physiol. Plantarium,*69:561–568 (Copenhagen).

Demmig–Adams et al., 1992, "Photoprotection and other Responses of Plants to High Light Stress", *Ann. Rev. Plant Physiol. Plant Mol. Biol.*, 43:599–626.

Zeevaart et al., 1988, "Metabolism and Physiology of Abscisic Acid", *Ann. Rev. Plant Physiol. Plant Mol. Biol.*, 39:439–473.

Rock et al., 1991, "The aba mutant of *Arabidopsis thaliana* is impaired in epoxy–carotenoid biosynthesis", *Proc. Natl. Acad. Sci. USA*, 88:7496–7499.

Mathews–Roth et al, 1991, "Effects of Carotenoid Administration on Bladder Cancer Prevention", *Oncology*, 48:177–179.

Palozza and Krinsky, "Antioxidant Effects of Carotenoids in Vivo and in Vitro: An Overview", 1992, *Methods Enzymol.*, 213:403–419.

Britton, 1988, "Biosynthesis of Carotenoids", *Plant Pigments* (Academic Press, NY) pp. 133–180.

Dogbo et al., Oct. 1988, "Carotenoid biosynthesis: Isolation and characterization of a bifunctional enzyme catalyzing the synthesis of phytoene", *Proc. Natl. Acad. Sci. USA*, 85:7054–7048.

Chamovitz et al., 1992, "Molecular cloning and expression in *E. coli* of cyanobacterial gene coding for phytoene synthase . . . ", *FEBS* 296(3):305–310.

Bartley et al., Mar. 1992, "Tomato Gene Expressed during Fruit Ripening Encodes an Enzyme of Carotenoid Biosynthesis Pathway", *J. Biol. Chem.*, 267:5036–5039.

Bramley et al., 1992, "Biochem characterization of transgenic tomato plants in which carotenoid syn. has been inhibited . . . ", *Plant J.*, 2(3):343–349.

Linden et al.,1991, "Functional Complementation in *E. coli* of Diff. Phytoene Desaturase Genes and Analysis of Accumulated Carotenes", *Z. Naturforsch.* 46(c):1045–1051.

Pecker et al., Jun. 1992, "A single polypeptide catlyzing the conversion of phytoene to ζ–carotene is transcriptionally regulated during tomato ripening", *Proc. Natl. Acad. Sci. USA*, 89:4962–4966.

Hugueney et al., 1992, "Characterization and molecular cloning of a flavoprotein catalyzing the synthesis of phytofluene and ζ–carotene in capsium chromoplasts", *Eur. J. Biochem*, 290:399–407.

Bramley, 1985, "The in Vitro Biosynthesis of Carotenoids", *Adv. Lipid Res.*, 21:243–279.

Armstrong et al., 1989, "Nucleotide seq., org. and nature of protein products of carotenoid biosynthesis gene cluster of *Rhodobacter capsulatus*", *Mol. Gen. Genet.*, 216:254–268.

Misawa et al, "Elucidation of *Erwinia uredovora* Carotenoid Biosyn. Pathway by Functional Analysis of Gene Products Expressed in *E. coli*", *J. Bacteriol.*, 172:6704–6712, 1990.

Hundle et al., "In vitro expression and activity of lycopene cyclase and β–carotene hydroxylase from *Erwinia herbicola*," FEBS, 315:329–334.

Ray et al., "Sequence of pTom5, a ripening related cDNA from tomato", 1987, *Nucleic Acids Res.*, 15:10587–10588.

Chamovitz et al., "The molecular basis of resistance to the herbicide norfluazon", 1991, *Plant Mol. Biol.*, 16:967–974.

Pecker et al., 1993, "Molecular Characterization of Carotenoid Biosyn. in Plants: Phytoene Desaturase Gene in Tomato", *Research in Phtosyn.* 3:11–18.

Bartley et al., Aug. 1991, "Molecular cloning & expression in photosynthetic bacteria of soybean cDNA coding for phytoene desaturase . . . " *Proc. Natl. Acad. Sci. USA*, 88:6532–6536.

Sandman et al., 1989, "Enzyme–Kinetic studies on Interaction of Norfluazon with Phytoene Desaturase", *Z. Natursorsch*, 44(C):787–790.

Chamovitz et al., 1990, "Cloning a Gene Coding for Norflurazon Resistance in Cyanobacteria", *A. Naturforsch*, 45(C):482–486.

Sandmann and Boger, 1989, "Inhibition of Carotenoid Biosynthesis by Herbicides", in *Target sites of herbicide acton* (CRC Press, Florida) pp. 25–44.

Yokoyama et al, 1982, "Chemical Regulation of Carotenoid Bioshynthesis" in Carotenoid Chem. and Biochem. (Pergamon Press, Oxford)pp. 371–385.

(List continued on next page.)

*Primary Examiner*—Elizabeth F. McElwain
*Attorney, Agent, or Firm*—Kohn & Associates

[57] ABSTRACT

A purified and isolated DNA sequence encoding lycopene cyclase.

23 Claims, 6 Drawing Sheets

PUBLICATIONS

Cunningham, 1985, "Carotenoids of Euglena Gracilis Klebs var. bacillaris Cori: Photoisomerization, Biosyn., Localixzation/Assoc. with chlorophylls/Polypeptides in chlorophyll--Protein Compl." (Dissertation).

Beversdorf et al., –"Registration of Triazine–Resistant Brassica Campestris Germplasm", *Crop Science*, 20:289.

Bucholtz et al., 1977, "Effects of In Vivo Inhibitors of Carotene Biosynthesis on Synthesis of Carotenes by Soluble Tomato . . . " *Chem. Biol. Interactions*, 17:359–362.

Beyer et al., 1980, "β–Carotene Synthesis in Isolated Chromoplasts from *Narcissus pseudonarcissus*", *Planta*, 150:435–438.

Camara and Moneger, 1992, "Biosynthetic capabilities and localization of enzymatic activities in carotenoid metabolism . . . ", *Physiol. Veg.*, 20:757–773.

Fosket et al., 1983, "Induction of Carotenogenesis in Cultured Cells of Lycopersicon Esculentum", *Plant Sci. Lett.*, 30:165–175.

Hsu and Yokoyama, "Carotenoid Biosynthesis in *Blakeslea trispora*", *Phytochemistry*, 11:2985–2990.

Beyer, 1989, "Carotene Biosynthesis in Daffodil Chromoplasts: On Membrane–Integral Desaturation and Cyclization Reactions", in *Phys., Biochem., Genetics of Nongreen Plastids*, pp. 157–170.

Linden et al., 1993, "Isolation of Carotenoid biosynthesis gene coding for ζ–carotene desaturation . . . ", *FEMS Microbial. Lett.*, 106:99–104.

Bird et al., 1991, "Using Antisense RNA to Study Gene Function: Inhibition of Carotenoid Biosynthesis in Transgenic Tomatoes", *Biotechnology*, 9:635–639.

Hall et al., 1993, "Antisense inhibition of pectin esterase gene expression in transgenic tomatoes", *Plant J.*, 3:121–129.

Hirschberg et al., 1987, "Isolation and Characterization of Herbicide Resistant Mutants in Cyanobacterium Synechococcus R2", *A. Naturforsch.* 42c:102–112.

Sambrook et al., 1989, Molecular Cloning: *A Lab. Manual* (2nd Edition) Cold Spring Harbor Lab. Press, pp. 316–317; 326–328.

Williams, 1988, "Technique for Radiolabeling DNA Restriction Endonuclease Fragments to High Specific Activity", *Methods Enzymol.* 167:766–778.

Feinberg et al., 1983, "Technique for Radiolabeling DNA Restriction Endonuclease Fragments to High Specific Activity", *Anal. Biochem.* 132:6–13.

Del Sal et al., 1988, "One–tube plasmid DNA mini–preparation suitable for sequencing", *Nucleic Acids Res.*, 16:9878.

Hundle et al, 1991, "Carotenoids of *Erwinia herbicola* and an *E. coli* Strain Carrying the *Erwinia herbicola* Carotenoid Gene Cluster", *Photochem Photobiol.*, 54:89–93.

Misawa et al. 1990, "Production of β–carotene in *Zymomonas mobilis* and *Agrobacterium tunefaciens* . . . ", *Appl. Environ. Microbiol.*, 57:1847–1849.

Sandman et al., 1990, "Identification of carotenoids in *Erwinia herbicola* and in transformed *E. coli* strain," *FEMS Microbiol. Lett*, 71:77–82.

Schnurr et al., 1991, "Mapping of carotenogenic gene cluster from *Erwinia herbicola* and functional identification of six genes", *FEMS Microbiol. Lett.*, 78:157–162.

Williams, 1988, "Construction of Specific Mutations in Photosystem II Photosyn. Reaction Center . . . ", *Methods Enzymol.*, 167:766–788.

Golden, 1988, "Mutagenesis of Cyanobacteria by Classical and Gene–Transfer–Based Methods", *Methods Enzymol.*, 167:714–7277.

Hawley et al., 1983, "Compiliation and analysis of *E, coli* promoter DNA sequences", *Nucleic Aids Res.*, (IRL Press Ltd. Oxford, England) 11:2237–2244.

Cunningham et al., Aug. 1993, "Cloning and functional expression in *E. coli* of cyanobacterial gene for lycopene cyclase, the enzyme that catalyzes biosyn of β–carotene", *FEBS*, 328:130–138.

```
                        A  A                          S
FAD CONSENSUS:   pssssGGG*GGsss******s*ssa
                 ||||||||| |||  |  |       | |||
lcy GENE PRODUCT: DALVIGSGPAGLAIAAELAQRGLKVQGLS
```

LYCOPENE CYCLASE GENE

This is a continuation-in-part of application Ser. No. 08/142,195 filed on Oct. 25, 1993, (now abandoned).

GRANT SUPPORT

This work was supported in part by the a grant from Hebrew University of Jerusalem to Joseph Hirschberg; by NSF career advancement award (#9008880) and a grant from the Maryland Agricultural Experiment Station to Elisabeth Gantt.

TECHNICAL FIELD

The present invention relates to the isolation of the DNA sequence for lycopene cyclase, and its regulatory sequences, and the use of the DNA sequence or regulatory sequences in preparing native and transgenic organisms in which the production of β-carotene and other carotenoids is controlled by the presence of the DNA sequence or to modify the expression of native genes.

BACKGROUND OF THE INVENTION

Carotenoids are the largest class of pigments in nature. They are synthesized de novo only in photosynthetic organisms and in several bacteria and fungi. Their essential function in plants is that of protecting against photooxidative damage sensitized by chlorophyll in the photosynthetic apparatus (Koyama, 1991; Siefermann-Harms, 1987), but they play a variety of other roles as well. They serve as accessory pigments in light-harvesting for photosynthesis and are integral components of photosynthetic reaction centers. Carotenoids are involved in the thermal dissipation of light energy captured by the light-harvesting antenna (Demmig-Adams et al., 1992), are substrates for the biosynthesis of the plant growth regulator abscisic acid (Zeevaart et al., 1988; Rock et al., 1991), and are the coloring agents of many flowers, fruits and animals. Certain cyclic carotenoids, including β-carotene, are precursors of vitamin A in human and animal diets and are of current interest as anticancer agents (Mathews-Roth et al., 1991; Palozza et al., 1992).

The generally accepted pathway of carotenoid biosynthesis in plants (Britton, 1988) begins with the head-to-head condensation of two molecules of the soluble 20 carbon compound geranylgeranyl pyrophosphate to give the colorless, membrane-bound carotenoid phytoene (FIG. 1). This two-step reaction in plants and cyanobacteria is catalyzed by a single, soluble enzyme: phytoene synthase (Dogbo, 1988; Chamovitz et al.; Linden, 1991; Pecker et al., 1992). Two sequential desaturations of phytoene result in the formation of first phytofluene and then ζ-carotene. Both of these reactions are carried out by a single enzyme in plants and cyanobacteria - phytoene desaturase (Linden et al., 1991; Pecker et al., 1992; Hugueney et al., 1992). This enzyme, and enzymes catalyzing subsequent steps in the pathway, are believed to be membrane-bound (Bramley, 1985). Two additional desaturations yield the symmetrical red carotenoid pigment lycopene, which is then converted to the yellow ζ-carotene via cyclization reactions at each end of the molecule (FIG. 1). Subsequent reactions in the pathway involve the addition of various oxygen functions to form the xanthophylls or oxygenated carotenoids.

Despite many efforts, few of the enzymes or genes of the carotenoid biosynthetic pathway have been identified and isolated in oxygenic photosynthetic organisms. The difficulties of preserving catalytic activity during purification of these largely membrane-bound enzymes have proven formidable, and the unavailability of labelled substrates for enzyme assay is also an obstacle.

Genes for the complete carotenoid biosynthetic pathways in the photosynthetic bacterium *Rhodobacter capsulatus* (Armstrong et al., 1989) and the nonphotosynthetic bacteria *Erwinia uredovora* (Misawa et al., 1990) and *Erwinia herbicola* (Hundle et al., 1993) have been cloned and sequenced. It was initially thought that such genes would provide molecular probes enabling the identification of homologous genes in oxygen-evolving photosynthetic organisms (cyanobacteria, algae, and plants). However, this approach has not proven fruitful because the Rhodobacter and Erwinia gene products bear little or no resemblance to the corresponding enzymes in oxygenic photosynthetic organisms (Pecker et al, 1992; Armstrong, 1994).

Two genes, those for phytoene synthase (Chamovitz et al., 1992; Ray et al., 1987) and phytoene desaturase (Pecker et al., 1992, 1993; Hugueney et al., 1992), have now been cloned from oxygenic photosynthetic organisms using other approaches. There is high conservation in the amino acid sequences of the cyanobacterial phytoene desaturase and the gene product of eukaryotic algae and higher plants (Pecker et al., 1992, 1993), but very little resemblance to the known bacterial or fungal phytoene desaturases.

The transformable cyanobacterium *Synechococcus sp.* PCC7942 is used herein as a model organism to study the carotenoid biosynthetic pathway in oxygen-evolving photosynthetic organisms. Applicants earlier cloned genes for phytoene synthase (psy, formerly called pys) and phytoene desaturase (pds) in this organism (Chamovitz et al., 1991; Chamovitz et al., 1992) and subsequently identified cloned and sequenced plant and algal genes using the cyanobacterial genes as probes (Pecker et al., 1992, Chamovitz et al., 1991; Pecker et al., 1993; Bartley et al., 1991.) The gene pds was identified with the aid of a bleaching herbicide, norflurazon, that specifically inhibits the desaturation of phytoene by interacting with the enzyme phytoene desaturase (Sandmann, 1989a). It was reasoned that a point mutation in the gene encoding the enzyme, leading to an amino acid substitution in the polypeptide, could confer resistance to the herbicide. By selecting for chemically-induced mutants which are resistant to norflurazon, and then mapping these mutations by genetic complementation of the resistance in the wild-type strain, applicants located the gene for phytoene desaturase (Chamovitz, 1990; Chamovitz et al., 1991).

It would be useful to be able to modify carotenoid synthesis to improve the nutritional value, pharmacology and appearance of plants. In so doing there are considerations which favor utilizing native genes where possible. In order to directly incorporate bacterial-origin genes in plants, the genes may require further modification to be able to be used, for example, in regulating the photosynthetic pathway. Further, bioengineered plants require regulatory approval prior to release to the environment. The regulatory process is more difficult if foreign genes are present. It would be more efficient to utilize the native genes, or DNA sequences, in controlling, for example, the β-carotene pathway.

Further, it would be useful to have available crops that are tolerant to herbicides that target the action of lycopene cyclase. Herbicides that target the carotenoid pathway may be of low toxicity since this pathway does not occur in humans, animals or insects. Further, plants that are herbicide tolerant at two loci within the carotenoid pathway would offer the potential for alternating applications of two herbicides thereby minimizing the appearance and selection of herbicide tolerant weed species.

SUMMARY OF THE INVENTION AND ADVANTAGES

According to the present invention, a DNA sequence encoding lycopene cyclase, has been purified and isolated. Both the genomic DNA sequence (SEQ ID No:1 ) from a cyanobacteria and cDNA sequence from tobacco (SEQ ID No:4) and tomato (SEQ ID No:5) have been purified and isolated.

The present invention further includes the method of manipulating the expression of native genes thereby not requiring the presence of foreign genes in the organism.

The present invention further includes the method of expressing the biosynthetic pathway from geranylgeranyl pyrophosphate to β-carotene in a suitable host cell, selected from eucaryotic and procaryotic cells, by incorporating the sequences encoding the enzymes controlling the pathway, including the sequence for lycopene cyclase. This method can be used to produce β-carotene in an organism not presently producing β-carotene thereby increasing the nutritional value, pharmacology or visual appearance value of the organism.

The present invention further includes the method for regulating expression of lycopene cyclase in transgenic organisms, constitutively or in a tissue-specific manner, to control the content of β-carotenetene or other carotenoids following in the biosynthetic pathway.

The present invention also includes a transgenic organism wherein the anti-sense expression of the sequence for lycopene cyclase, is incorporated into the genomic DNA thereby inhibiting the synthesis of lycopene cyclase and accumulating the red pigment lycopene. This method can provide a red color to an organism not previously red or deepen the red appearance of a presently red organism.

Finally, the present invention also includes the construction of transgenic plants that are resistant to the action of herbicides such as the herbicide MPTA and other related compounds of the trialkylamines and other herbicides which interact with the lycopene cyclase enzyme.

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE PREFERRED EMBODIMENT

The present invention consists of a DNA sequence that encodes the enzyme lycopene cyclase (LCY) as best shown in SEQ ID No:1, SEQ ID No:4 and SEQ ID No:5. The present invention further can include at least one additional DNA sequence flanking the DNA sequence as best shown in SEQ ID No:1. This flanking sequence can be a promoter.

The sequence can be the gene, and which has been purified, isolated and cloned from a cyanobacteria (SEQ ID No:1). The sequence also includes cDNA and which has been isolated for tobacco (SEQ ID No:4) and tomato (SEQ ID No:5) for example.

Figure 1:
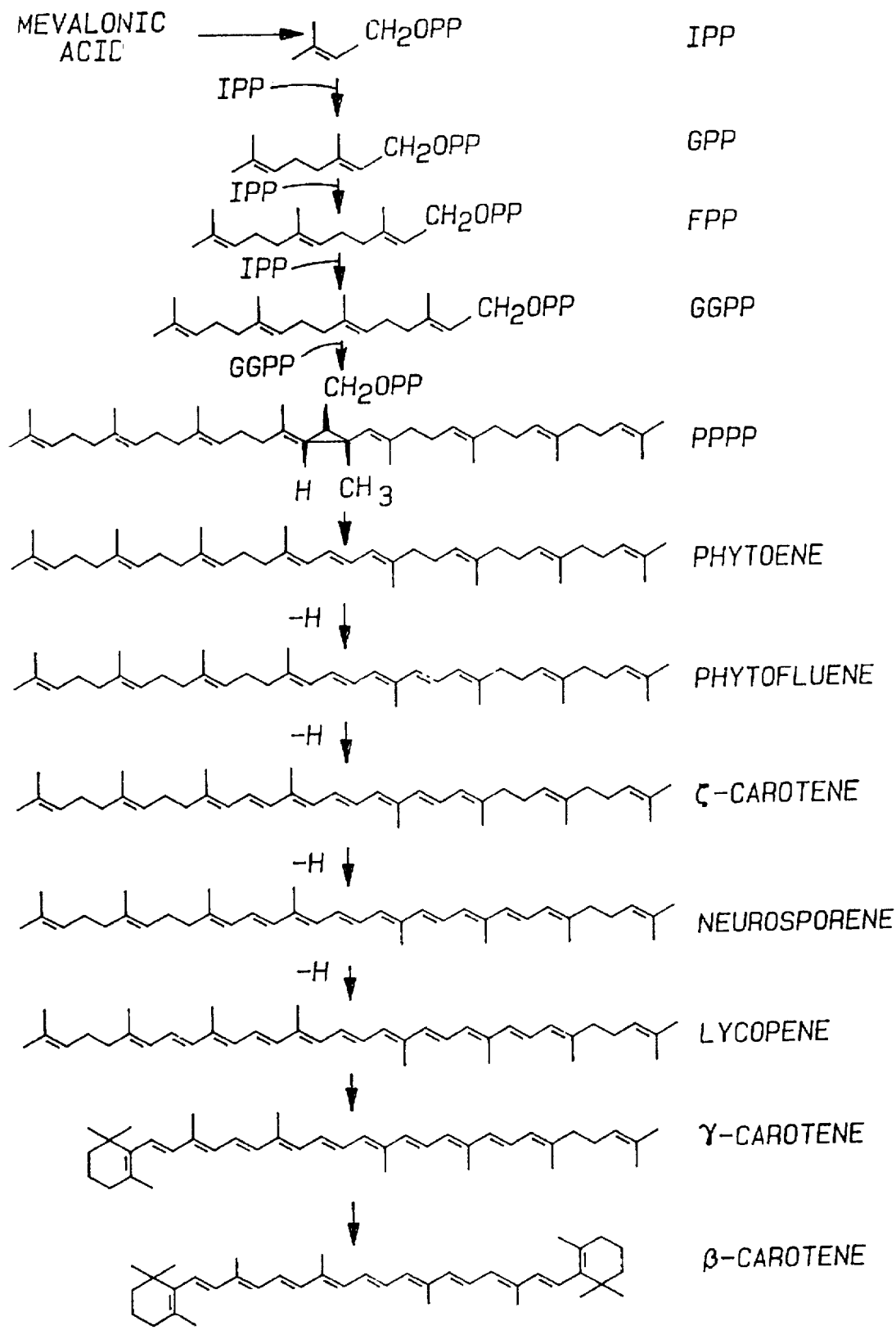
FIG. 1 is a diagram of the carotenoid biosynthetic pathway in cyanobacteria and plants (IPP=isopentenyl pyrophosphate; GPP=geranyl pyrophosphate; FPP=farnesyl pyrophosphate; GGPP=geranylgeranyl pyrophosphate; PPPP=prephytoene pyrophosphate)
Figure 2:
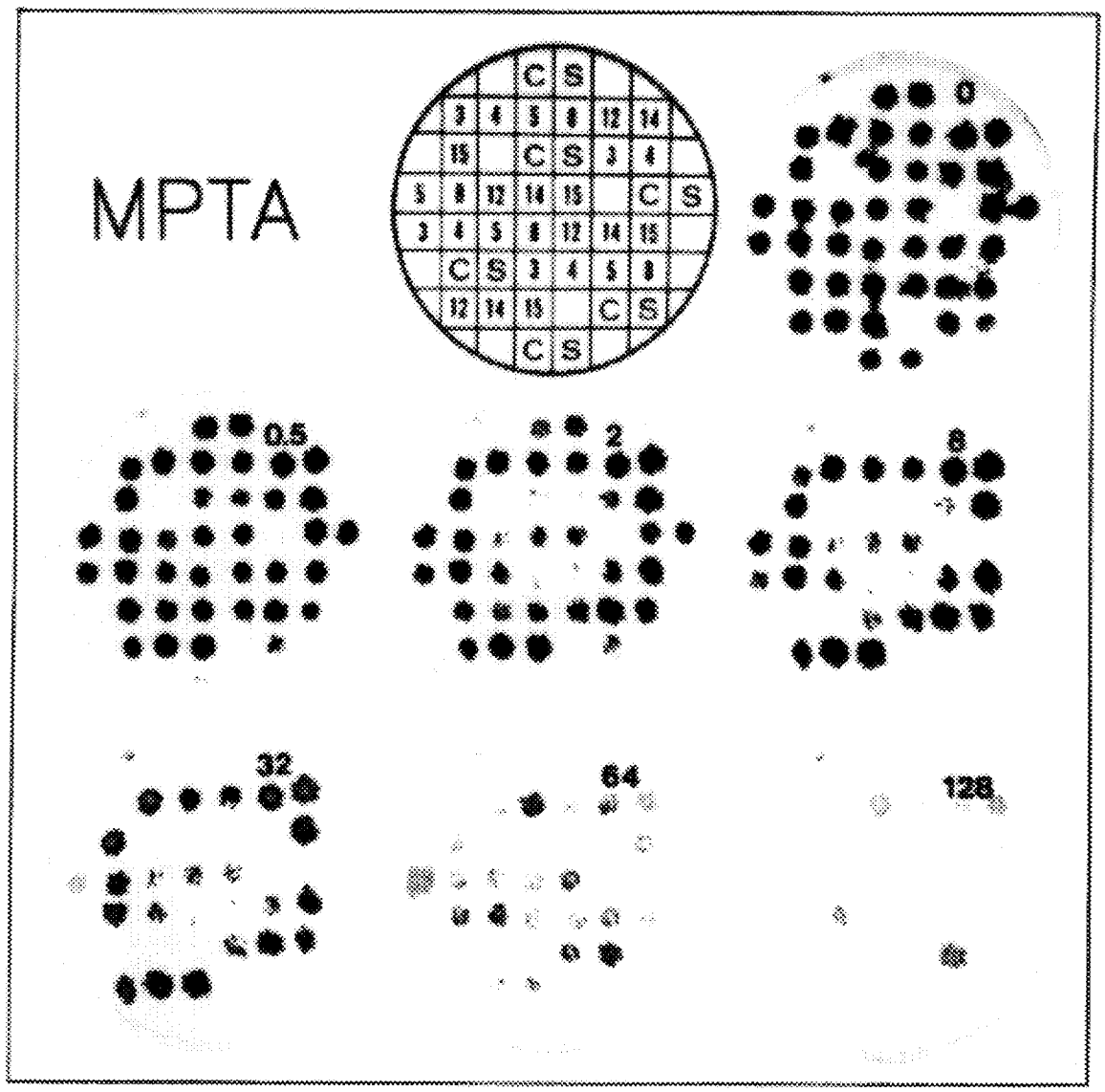
FIG. 2 is a photograph of petri dishes showing MPTA-resistance in mutants (numbered) and two wild-type strains (C and S) of the cyanobacterium *Synechococcus sp.* PCC 7942, the wild-type strain indicated by the letter C was the parent strain from which the mutants were derived, the concentration of MPTA, in micromolar, is given in the upper right corner of each petri dish, and each strain was spotted in several places on each petri dish because of a modest positional influence on survival.
Figures 7, 8:
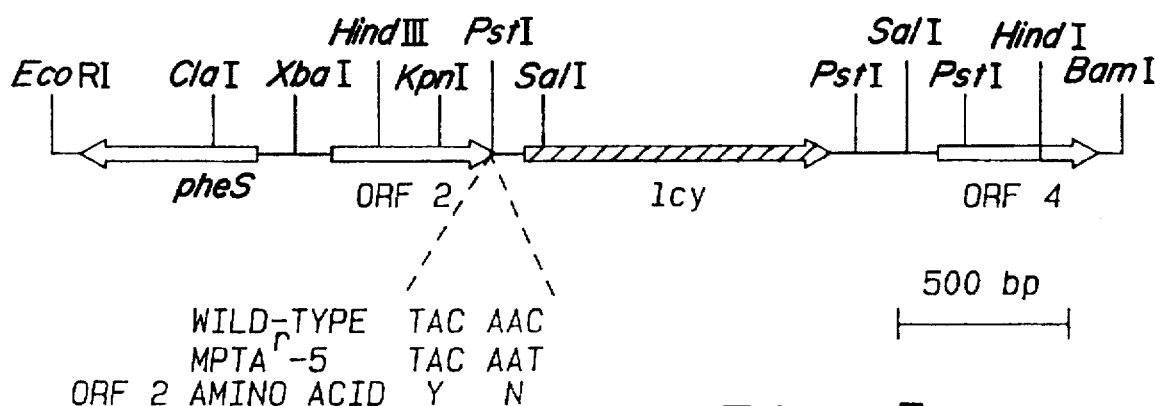
FIG. 7 is a diagram showing the identification of a mutation for MPTA resistance within the promoter region upstream of the lycopene cyclase gene.
FIG. 8 is a diagram showing a dinucleotide-binding motif at the amino terminus of LCY indicating that FAD is utilized by lycopene cyclase (a is acidic: D or E, p is polar or charged: D,E,K,R,H,S,T,Q,N, s is small or hydrophobic: A,I,L,V,M,C, and * is any amino acid).

The sequence for lycopene cyclase can either be the wild type or can be modified by point mutations, deletions or insertions such that the resulting sequence is altered imparting herbicide resistance. The modification can be in either the DNA sequence that encodes the enzyme lycopene cyclase (LCY) or in the flanking sequence. A sequence consisting of a modified DNA sequence in the promoter region of the gene for lycopene cyclase conferring resistance to MPTA was also purified, isolated, cloned and sequenced in the practice of the present invention (FIGS. 2 and 7).

Vectors carrying the DNA sequences as set forth above can also be prepared in the practice of the present invention using methods set forth in the Methods section hereinbelow. Host cells, wherein the host cell is selected from the group of eucaryotic and procaryotic cells which can be transformed with these vectors, can also be prepared in the practice of the present invention. The host cells can be *E. coli*, cyanobacteria such as Synechococcus PCC7942 and Synechocystis PCC6803(Available from the American Tissue Culture Collection, 12301 Parklawn Drive, Rockville, Md 20852 as catalog numbers 33912 and 27084 respectively), alga and plant cells. Suitable host cells include a carotenogenic organism if only the sequence for lycopene cyclase is used or cells that contain phytoene, the precursor for pds or crtI gene products and are host cells which can be transformed by the vector being used.

In the practice of the present invention, transgenic organisms can be constructed which include the DNA sequences as set forth hereinabove that are incorporated into the genomic DNA (Bird et al, 1991; Bramley et al, 1992; Misawa et al, 1994b; Misawa et al, 1994a). The incorporation of these sequences can allow the controlling of carotenoid biosynthesis, content, composition or amount in bacteria, algae, and plants. These transgenic organisms can be constructed to incorporate sequences which allow overproduction of lycopene cyclase (Cunningham et al, 1993, 1994), i.e. production over the amount normally present in a cell. In a further embodiment, the transgenic organisms can also incorporate sequences which confer herbicide-resistance thereby producing an herbicide-resistant organism, and in a preferred embodiment resistance to bleaching herbicides of the trialkylamine family including CPTA and MPTA. Other modifications can be introduced to alter regulation of carotenoid biosynthesis.

Transgenic organisms can also be constructed in the present invention wherein the anti-sense expression of the DNA sequence for lycopene cyclase is incorporated into the genomic DNA thereby inhibiting the synthesis of lycopene cyclase and accumulating the red pigment lycopene. Further, in the process of controlling carotenoid biosynthesis, content, composition or amount in bacteria, alga, and plant vectors can be prepared of a DNA sequence consisting of an anti-sense expression of the DNA sequence for lycopene cyclase and these vectors used in transforming cells of bacteria, algae, and plants thereby forming transgenic organisms (Gray et al, 1994; Hall et al, 1993).

Applicants have recently proposed changing the nomenclature referring to the gene encoding for lycopene cyclase from lcy to crtL in all species. The crt nomenclature originated for the *R. capsulatus* genetic loci required for carotenoid biosynthesis and has been maintained for *Rhodobacter species, Erwinia species* and *Thermus thermophilus*. Genetic loci involved in carotenoid biosynthesis in M. xanthus have been designated car in a parallel nomenclature. In higher plant species the genes were named as abbreviations of the enzyme formed. Applicants have proposed adopting the crt nomenclature for higher plants. Accordingly, as used herein lcy and crtL are equivalent designations. (See Armstrong, 1994, Table I for a comparison of the various nomenclatures.)

Herbicides are generally effective by disrupting selected biochemical pathways. Herbicides that interfere with the carotenoid biosynthetic pathway are particularly effective. These herbicides include a number of substituted triethylamine compounds that inhibit the formation of cyclic carotenoids and result in the accumulation of lycopene in plants, algae, and cyanobacteria (Sandmann et al., 1989b). A particularly effective inhibitor of this class is the compound 2-(4-methylphenoxy)-triethylamine hydrochloride (MPTA) (Yokoyama et al., 1992; Cunningham, 1985). The target site of MPTA and related compounds is believed to be the enzyme lycopene cyclase (Sandmann et al., 1989b).

Applicants have described isolated MPTA-resistant mutants of *Synechococcus sp.* PCC 7942 and cloned a gene that contains one of the mutations (see FIG. 7). Expression of this gene in a lycopene-accumulating strain of *E. coli* showed unequivocally that the MPTA-resistance gene encodes lycopene cyclase. DNA hybridization analysis indicates that the sequence of this gene is conserved among other photosynthetic eukaryotes.

Mutations imparting herbicide resistance can be point mutations, deletions or insertions. The mutations can occur either within the nucleotide sequence of lycopene cyclase, designated crtL (originally designated lcy) such that the resulting amino acid sequence is altered imparting herbicide resistance or within the flanking sequences of crtL such that regulation of the expression of crtL is altered imparting herbicide resistance. An example of the latter mutation is that of mutant 5 as shown in FIG. 7. In this mutant, a single base change (base number 1925 in SEQ ID No:1) in the promoter region of crtL, 104 base pairs upstream of the initiation codon, changes a C to a T and confers a high degree of herbicide-resistance to cells of Synechococcus which contain it (see FIG. 2), presumably by greatly increasing biosynthesis of the enzyme.

In cloning the gene for lycopene cyclase, the strategy that was used earlier to identify the gene for phytoene desaturase in *Synechococcus sp.* PCC7942 was used. The rationale for this approach is derived from the assumption that the enzyme lycopene cyclase is the target site of the bleaching herbicide MPTA, and the conjecture that a subtle change in the primary structure of lycopene cyclase could produce an enzyme that was tolerant of MPTA and yet still retain adequate catalytic activity. Applicants did not know, a priori, whether the resistant phenotype of a particular mutant was derived from a lesion in the gene for lycopene cyclase. The phenotype selected could as well have been due to an increase in the rate of breakdown or detoxification of the herbicide, or the result of a reduction in herbicide uptake. The functional expression in *E. coli* of a gene that contains the MPTA-resistance mutation of mutant M'-5 demonstrated that this gene, originally designated lcy, does, in fact, encode the enzyme lycopene cyclase. A number of other MPTA resistance mutations have been mapped to the lcy gene. The wild-type gene product (Seq. ID No. 2) and those of these other mutants also function well in *E. coli*.

Lycopene is the primary substrate for the formation of cyclic carotenoids in plants and cyanobacteria. The conversion of lycopene to β-carotene requires that cyclization reactions occur at both ends of the symmetrical lycopene. The present invention demonstrates that a single cyanobacterial enzyme efficiently catalyzes both cyclizations. Accumulation of the monocyclic species γ-carotene in cultures, as described hereinbelow, was not observed in the absence of herbicide, even though a substantial amount of lycopene as well as β-carotene, accumulated in these cells. This observation indicates that any molecule of lycopene which is cyclized at one end has a very high probability of being cyclized at the other end as well. The possibility that lycopene cyclase operates as a homodimeric complex is one explanation for these results.

As part of the isolation and for use in transformation procedures, novel plasmid pLYCB-M5XE was constructed and described herein. Plasmids pLCYB-M5PPF, and pLYCB-M5SP are truncated versions of pLCYB-M5XE and are described herein. The various plasmids were constructed as described in the materials and methods section below.

Using the present invention, it is possible to transform host cells, including *E. coli*, cyanobacteria, algae and plants, using the appropriate vectors so that they carry either the DNA sequence for lycopene cyclase or the mutated sequence of DNA for lycopene cyclase that is resistant to MPTA. Such transformed cells allow the regulation of the lcy gene and regulation of the catalytic function of LCY.

Applicants observed that no cyclization of $\zeta$-carotene takes place when lcy is expressed in cells of *E. coli* that accumulate $\zeta$-carotene. This result implies that the cyclization reactions catalyzed by the Synechococcus lcy gene product require that the linear molecule be fully desaturated. It was shown in Phycomyces that neurosporene can undergo cyclization only in that half of the molecule which is desaturated to the level of lycopene (Bramley, 1985).

The present invention includes the construction of transgenic organisms that are resistant to MPTA and other herbicides that interfere with the cyclization of lycopene. The agronomical advantage of using an herbicide resistant crop has been demonstrated in the *Brassica species*, including *B. napus*, where atrazine resistance was introduced by genetic crossing of the crop with a weed of the same genus (Beaversdorf et al., 1980).

The target site of action for MPTA and related compounds has been a matter of some dispute. MPTA was previously shown to induce accumulation of lycopene in grapefruit (Yokoyama, 1982) and to prevent cyclization of lycopene in isolated chloroplasts of *Euglena gracilis* (Cunningham, 1985). Much more work has been done with the structurally-related compound 2-(4-chlorophenylthio)-triethylamine hydrochloride (CPTA) (Sandmann et al., 1989b) with similar results: lycopene accumulation in vivo. However, in contrast to the results obtained in vivo, CPTA has been reported to exert little or no effect on carotenoid biosynthesis in cell-free systems derived from acetone extracts of tomato plastid (Bucholtz et al., 1977), from *Narcissus chromoplasts* (Beyer et al., 1980) and from *Capsicum chromoplasts* (Camara et al., 1982). Suggestions have been made that CPTA and related compounds act at the level of gene expression rather than by directly affecting enzyme function (Bucholtz et al., 1977; Fosket et al., 1983; Hsu et al., 1972).

More recent work, using a cell-free system from the cyanobacterium Aphanocapsa, indicates that CPTA can be an effective inhibitor of lycopene cyclization in vitro and that it inhibits the cyclization reaction in a noncompetitive manner as reviewed by Sandmann et al. (1989b). The lack of inhibition by CPTA observed in many other cell-free systems suggests that the physical integrity of the membrane and/or an ordered structural association of the enzymes of carotenoid biosynthesis are important for effective herbicide action. The fragile nature of the carotenoid biosynthetic machinery in cell free systems is well known (Beyer, 1989).

The finding herein that a mutation in the gene for lycopene cyclase confers resistance to MPTA provides strong evidence that this enzyme is a target site of action for MPTA and related compounds can be made but it is not to be construed as limiting the present invention to this one mode of action. This conclusion is further supported by the observation that MPTA inhibits lycopene cyclase activity in cells of *E. coli* where no authentic cyanobacterial carotenogenic apparatus is presumed. The accumulation of $\gamma$-carotene in MPTA treated cells of *E. coli* suggests that the second cyclization step carried out by lycopene cyclase is more sensitive to inhibition by the herbicide. These findings make possible the transformation of crop plants to be MPTA resistant by insertion of any of applicants' many different MPTA'-mutant lycopene cyclase genes. More importantly, the present invention can be used to guide the bioengineering of native plant and algal genes for resistance to MPTA and other herbicides.

Southern hybridization analysis, using the cyanobacterial crtL sequence as a molecular probe, indicates that this gene sequence is conserved with similar DNA sequences in eukaryotic alga, and predicted the feasibility of using crtL as a molecular probe to clone lycopene cyclase from algae and higher plants. The isolation of cDNA for lycopene cyclase from tobacco and tomato confirms this utility. It further indicates that transgenic plants carrying the present invention will be functional. The fact that higher plants contain a lycopene cyclase gene that has a sequence similar to crtL indicates that, as in the cases of the genes for phytoene synthase and phytoene desaturase, the enzymology of lycopene cyclization in plants is similar to cyanobacteria and distinct from other microorganisms. This implies that crtL, by being analogous to the plant homolog, will be functional when expressed in transgenic algae or plants.

In the "plant-type" pathway of carotenoid biosynthesis, applicants have identified genes for all of the steps from geranylgeranyl pyrophosphate to $\beta$-carotene except the two desaturations which convert the symmetrical $\zeta$-carotene to lycopene. Cloning of a putative gene for $\zeta$-carotene desaturase has been recently reported (Linden et al., 1993). The desaturation of $\zeta$-carotene in plants and algae is inhibited by a number of experimental bleaching herbicides (Sandmann et al., 1989b), and several of these compounds effectively inhibit the desaturation of $\zeta$-carotene in Synechococus PCC7942 (Sandmann et al., 1989b). Applicants' successes in cloning psy, pds, and the present invention, crtL (lcy), using techniques known in the art, indicate that the same strategy of mutagenesis and selection of herbicide-resistant mutants derived under the scope of the invention will enable the cloning of $\zeta$-carotene desaturase with the appropriate inhibitors. From this, the present invention allows the construction of the biosynthetic pathway from geranylgeranyl pyrophosphate to $\beta$-carotene in a suitable host cell by incorporating the DNA sequence encoding for psy, pds, zds and lcy.

The present invention also includes a transgenic organism wherein the anti-sense expression of the crtL gene is incorporated into the genomic DNA thereby inhibiting the synthesis of lycopene cyclase and accumulating the red pigment lycopene. This method can provide a red color to an organism not previously red or deepen the red appearance of a presently red organism. The use of antisense technology to alter gene expression to modify a plant's phenotype has been developed and is now available to those skilled in the art. This technology has been utilized with tomatoes, including the carotenoid biosynthesis pathway (Bramley, 1992; Bird et al., 1991; Hali et al., 1993, U.S. Pat. No. 5,304,490).

The examples hereinbelow illustrate the methods of isolation, purification and cloning of the respective crtL sequences as well as probe/vector construction and use. Further examples demonstrate the use of the vectors to transform suitable host cells such as bacteria, algae and plants, as well as determining the sites of herbicide resistance. Suitable host cells include a carotenogenic organism if only lcy is used or cells that contain phytoene, the precursor for pds or crtI gene products and are host cells which can be transformed by the vector being used.

In summary, the use of the cyanobacterium Synechococcus PCC7942 as a model organism for studying the carotenoid biosynthetic pathway has provided findings obtained with this genetically simple and convenient organism that are broadly applicable to any oxygenic photosynthetic organism (plants, algae and cyanobacteria). That is, once a carotenoid biosynthesis gene is identified in Synechococcus, it is then possible to isolate a gene with sequence similarity from any plant or alga. This has been demonstrated by the applicants' use of the Synechococcus gene for phytoene desaturase to clone genes with sequence similarity from plants and algae. Where the plant or algal gene had not been identified, applicants' initial identification of the cyanobacterial gene provided the essential and sufficient tool that enabled identification and cloning of the plant and algal genes for phytoene desaturase. In the present application, identification of a lycopene cyclase gene from Synechococcus PCC7942 provides, in the same way, the necessary and sufficient tool to identify and clone algal and plant genes with sequence similarity such as from tomato (SEQ ID No:5) and tobacco (SEQ ID No:4). The Synechococcus lycopene cyclase gene, as those for pds and psy before it, bears little resemblance to the two known bacterial genes from Erwinia (Pecker et al., 1992; Armstrong, 1994) or to any other genes in the major databases (GenBank and SwissProt).

Modification of the native genes of plants and algae is now made possible (Bird et al., 1991; Bramley et al., 1992; Misawa et al., 1994b; Misawa et al., 1994a). For example, observations made with the cyanobacterial gene locate the sites of herbicide resistant mutations which can then be used in determining where to alter the native genes for herbicide-resistance. For any new herbicide that appears, resistant mutants are selected to determine what modifications of the amino acid sequence of the enzyme or regulatory DNA Sequences can confer the resistance. The native enzyme of any plant or regulatory sequence can be changed in the same way to produce the analogous mutant. In addition, the expression of the genes can be modified and manipulated in a tissue-specific manner and the use of antisense technology (Gray et al, 1994; Hall et al, 1993) with the native genes is also possible.

The above discussion provides a factual basis for the utility of the lycopene cyclase gene. The methods used with and the utility of the present invention can be shown by the following examples.

EXAMPLES

GENERAL METHODS

Organisms and Growth Conditions

Cultures of Synechococcus sp. PCC7942 (Anacystis nidulans R2) were grown in BG11 medium at 35° C. as described previously (Hirschberg et al., 1987). For selection of MPTA-resistant mutants (MPTA$^r$) and transformants, cultures were spread on solid BG11 medium containing 1.5% agar (Bacto) and 20 or 30 μM MPTA. The MPTA was added to molten agar at 50° C. from a 20 mM stock solution in MeOH immediately before pouring into petri dishes. Where required, kanamycin was incorporated in the BG11 agar plates at a concentration of 10 μg/ml.

Escherichia coli strain XL1-Blue was used as host for genomic libraries of Synechococcus in the plasmid vector pBR329K[25] with kanamycin at 30 μg/ml for selection, and as a host for the plasmid pBluescript II KS$^+$ (Stratagene) and other plasmids with ampicillin at 100 μg/ml and/or chloramphenicol at 50 μg/ml. Cultures of E. coli were grown in the dark at 37° C. in LB medium (Sambrook et al., 1989).

Selection of MPTA-Resistant Mutants Cultures of Synechococcus were treated with the chemical mutagen ethane methylsulfonate (EMS, Sigma Chemical Company, St. Louis, Missouri) as described previously (Hirschberg, 1987), and were allowed to grow for 24 hours in liquid culture before selection on BG11 agar plates containing 20 or 30 μM MPTA. Herbicide tolerance in the selected mutants was examined by spotting 3 μl of dilute cultures on a master petri dish of BG11 agar. After two weeks of growth, replicas were made on plates containing different concentrations of MPTA and allowed to grow for two more weeks. Mutants were maintained on BG11 agar plates containing 4 μM MPTA. The MPTA was a generous gift of Dr. Henry Yokoyama, Fruit and Vegetable Chemistry Laboratory, Agricultural Research Service, United States Department of Agriculture, Pasadena, Calif. 91106.

Molecular Cloning

Genomic DNA was extracted (Williams, 1988) from MPTA-resistant Synechococcus mutant number five (M$^r$-5), completely digested with EcoRI, and used to construct a genomic library in the EcoRI site of pBR329K (Chamovitz, 1990). The parent wild-type strain was transformed (Williams, 1988) with DNA of this M$^r$-5 library, and transformants were selected on BG11 agar plates containing both MPTA (20 or 30 μM) and kanamycin (10 μM). The strategy described in Chamovitz et al. (1990) was employed to recover the plasmid vector, along with flanking genomic DNA. A 2.1 kb EcoRI-SalI genomic DNA fragment, which was recovered in this way, was used as a molecular probe. $^{32}$P-labelling was carried out by the random priming method (Feinberg et al., 1983). An 8.5 kb genomic clone, identified by colony hybridization (Sambrook et al., 1989) using this probe, was subcloned in the plasmid pBluescript II KS$^+$ (Stratagene) and was designated pM5EE. Various fragments of this clone were subcloned in the vector pBluescript II KS$^+$ and their ability to transform the wild-type strain of Synechococcus sp. PCC7942 to MPTA resistance was tested. Plasmid DNA minipreps were prepared using the procedure of Del Sal et al. (1988).

Construction of a Lycopene-Accumulating Strain of E. coli

To demonstrate activity of lycopene cyclase (LCY) it was essential to modify cells of Escherichia coli by genetic engineering so that they will produce lycopene, which is the substrate of the enzyme LCY. Several examples of such an engineering in E. coli utilizing genes from Erwinia species have been published in the past (Misawa et al., 1990; Hundle et al., 1991; Hundle et al., 1993; Misawa et al., 1991; Sandmann et al., 1990; Schnurr et al., 1991). Briefly, the vector is constructed from a cluster of genes encoding carotenoid biosynthesis enzymes that has been cloned from Erwinia uredovora (Misawa et al., 1990). A 2.26 kb BstEII-SnaBI fragment was deleted from the plasmid pCAR (Misawa et al., 1990), and a 3.75 kb Asp718-EcoRI fragment, carrying crtE, crtB and crtI, was subcloned in the EcoRV site of the plasmid vector pACYC184. The resulting vector which has the same insert as the recombinant plasmid designated pCAR-ADE (Misawa et al., 1990) is then used to construct the lycopene-accumulating strain of E. coli.

Functional Expression of Lycopene Cyclase in E. coli

A 7.2 kb XbaI-EcoRI DNA fragment, containing the MPTA resistance mutation, was cloned in the multiple cloning site of the vector pBluescript II SK$^+$ (Stratagene) and then excised as a SacI-EcoRI fragment. This SacI-EcoRI fragment was then cloned in the IPTG-inducible expression vector pTrcHisB (Invitrogen) and the resulting plasmid, designated pLYCB-M5XE, was used to transform competent cells of the lycopene-accumulating strain of *E. coli* as described hereinabove. Transformed cells were plated on LB agar plates containing ampicillin (100 µg/ml) and chloramphenicol (50 µg/ml), and spread with 10 µl of a 100 mM aqueous solution of isopropylthio-β-D- galactoside (IPTG) one hour before cells were plated.

Carotenoid Pigment Analysis

Cultures of *E. coli* were grown for 18 hours at 37° C. in LB medium containing 1 mM IPTG. Bacterial cells from 50 ml of the suspension culture were harvested by centrifugation and carotenoid pigments were extracted by dissolving the pellet in 90% acetone. The carotenoids were analyzed by HPLC on a Spherisorb ODS1 25 cm reverse phase column as previously described (Chamovitz et al., 1992). A Merck/ Hitachi HPLC apparatus, consisting of a L6200 pump, L300 multichannel photodetector with D6000 interphase was used, employing an isocratic solvent system of acetonitrile/ methanol/isopropanol (85:10.5). The Hitachi DAD Manager software allowed for the simultaneous detection of phytoene and colored carotenoids. Individual carotenoids were identified on the basis of online absorption spectra and typical retention times in comparison to reference standards of lycopene and β-carotene.

Construction and delivery of vectors

Such vectors are known or can be constructed by those skilled in the art and should contain all expression elements necessary to achieve the desired transcription of the sequences. Other beneficial characteristics can also be contained within the vectors such as mechanisms for recovery of the nucleic acids in a different form. Phagemids are a specific example of such beneficial vectors because they can be used either as plasmids or as bacteriophage vectors. Examples of other vectors include viruses such as bacteriophages, baculoviruses and retroviruses, DNA viruses, cosmids, plasmids, liposomes and other recombination vectors. The vectors can also contain elements for use in either procaryotic or eucaryotic host systems. One of ordinary skill in the art will know which host systems are compatible with a particular vector.

The vectors can be introduced into cells or tissues by any one of a variety of known methods within the art. Such methods can be found generally described in Sambrook et al., *Molecular Cloning: A Laboratory Manual*, Cold Springs Harbor Laboratory, New York (1992), in Ausubel et al., *Current Protocols in Molecular Biology*, John Wiley and Sons, Baltimore, Md. (1989), Chang et al., *Somatic Gene Therapy*, CRC Press, Ann Arbor, Mich. (1995), Vega et al., *Gene Targeting*, CRC Press, Ann Arbor, MI (1995) and Gilboa, et al (1986) and include, for example, stable or transient transfection, lipofection, electroporation and infection with recombinant viral vectors. Introduction of nucleic acids by infection offers several advantages over the other listed methods. Higher efficiency can be obtained due to their infectious nature. Moreover, viruses are very specialized and typically infect and propagate in specific cell types. Thus, their natural specificity can be used to target the vectors to specific cell types in vivo or within a tissue or mixed culture of cells. Viral vectors can also be modified with specific receptors or ligands to alter target specificity through receptor mediated events.

Other molecular biology methods not expressly set forth

Such methods can be found generally described in Sambrook et al., *Molecular Cloning: A Laboratory Manual*, Cold Springs Harbor Laboratory, New York (1992), in Ausubel et al., *Current Protocols in Molecular Biology*, John Wiley and Sons, Baltimore, Md. (1989).

EXAMPLES

1. Selection and mapping of MPTA-Resistant Mutants.

Wild-type cells of the cyanobacterium *Synechococcus sp.* PCC7942 did not grow on BG11 agar plates containing more than 2 µM of the bleaching herbicide MPTA. Following mutagenesis of the wild-type strain with EMS and selection for growth on agar plates containing 30 µM MPTA, applicants selected a number of herbicide-tolerant mutants. Mutant number five ($M^r$-5) exhibited the highest resistance and grew on agar plates containing 50 µM MPTA (FIG. 2). This mutant was used for all subsequent experiments described in this application.

The genetic basis of MPTA resistance in $M^r$-5 was established by transformation experiments. Genomic DNA was extracted from $M^r$-5, digested with the endonuclease EcoRI and transfected to wild-type cells of Synechococcus PCC 7942. The appearance of colonies at high frequency (ca. $10^4$ times that for untransformed controls) on agar plates containing 30 µM MPTA demonstrated the genetic character of the resistance to MPTA and indicated that either a single lesion or closely-linked mutations were responsible for the resistance trait.

2. Cloning the MPTA-Resistance Gene.

A genomic library of mutant $M^r$-5 was constructed in the EcoRI site of the plasmid vector pBR329K (Chamovitz, 1990). DNA of this library was transfected to cells of the wild-type strain as closed circular plasmids, and transformants were selected for growth on BG11 agar plates containing both MPTA and kanamycin. Stable transformation in *Synechococcus sp.* PCC 7942 occurs by integration of the foreign DNA into the bacterial chromosome following homologous recombination (Williams, 1988; Golden, 1988). The doubly-resistant transformants resulted from a single cross-over event between a plasmid containing genomic DNA with the mutation for MPTA resistance ($MPTA^r$), and its homologous sequence in the chromosome. Consequently, the pBR329K plasmid DNA was integrated into the cyanobacterial chromosome adjacent to the MPTA-resistant gene (FIG. 2 in the 1990 Chamovitz et al. reference provides detailed explanation).

A portion of the pBR329K vector was recovered, along with a fragment of the adjacent genomic DNA, by digestion of the genomic DNA of a doubly-resistant transformant with either SalI or BamHI endonucleases, followed by DNA ligation reaction, transfection to cells of *E. coli*, and selection for kanamycin resistance ($Kan_r$). From one such $Kan^r$-$MPTA^r$ transformant, applicants recovered a 2.1 kb EcoRI-SalI fragment of cyanobacterial genomic DNA. This fragment was used as a molecular probe to screen the original $M^r$-5 genomic DNA library and identified a plasmid containing an 8.5 kb EcoRI genomic insert. Transfection of this 8.5 kb DNA fragment into cells of the wild-type strain of *Synechococcus sp.*

Figure 3:
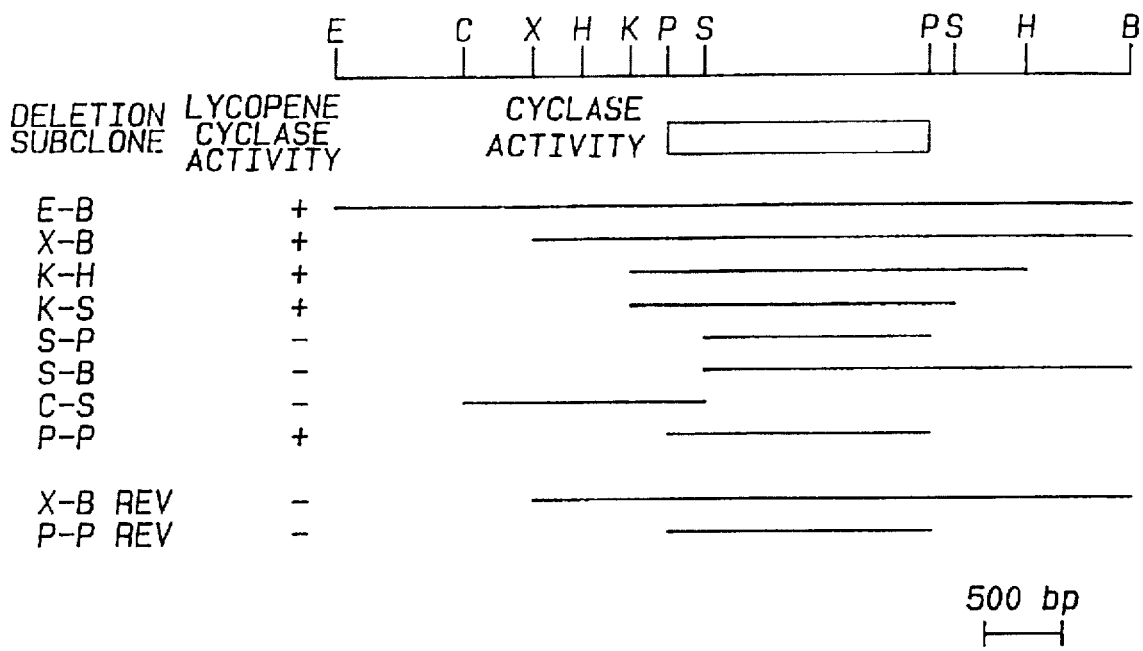
FIG. 3 is a diagram representing a map showing the mutation site of MPTA$^r$-5 (mutant 5) wherein various sub-fragment of the 4.6 kB EcoRI-BamHI genomic fragments (indicated below the restriction map) were cloned in the vector pBluescript KS$^+$ and transfected to cells of the wild-type strain of *Synechococcus sp.* PCC7942, and their ability to confer herbicide-resistance (indicated by +) was established by plating the transformants on MPTA containing medium (B=BamHI; C=ClaI; E=EcoRI; K=KpnI; H=HindIII; P=PstI; S=SalI; X=XbaI), rev=reverse orientation.

PCC7942 resulted in a high frequency of herbicide-resistant colonies, thus confirming that this fragment contained the mutation conferring $MPTA^r$. A similar test indicated that the mutation was located in a 4.6 kb EcoRI-BamHI fragment, and subsequently it was mapped to a region of 0.2 kb that is delineated by the PstI and SalI restriction sites (FIG. 3).

3. The MPTA Resistance Gene Encodes Lycopene Cyclase.

Since MPTA inhibits lycopene cyclization, applicants expected that the MPTA resistance in strain $M^r$-5 was due to a change in lycopene cyclase, so that mapping the mutation would lead to the gene for this enzyme. Applicants, therefore, tested for the presence of this gene by expressing cyanobacterial genomic fragments containing the mutation, in cells of *E. coli* that produce lycopene.

The constructed plasmid, as described hereinabove (Misawa et al., 1990), was used which contained genes from the bacterium *E. uredovora* encoding the enzymes GGPP synthase (crtE), phytoene synthase (crtB) and phytoene desaturase (crtI). Cells of *E. coli* carrying this plasmid accumulate lycopene (FIG. 6) and produce pink colonies on agar plates.

Figure 4:
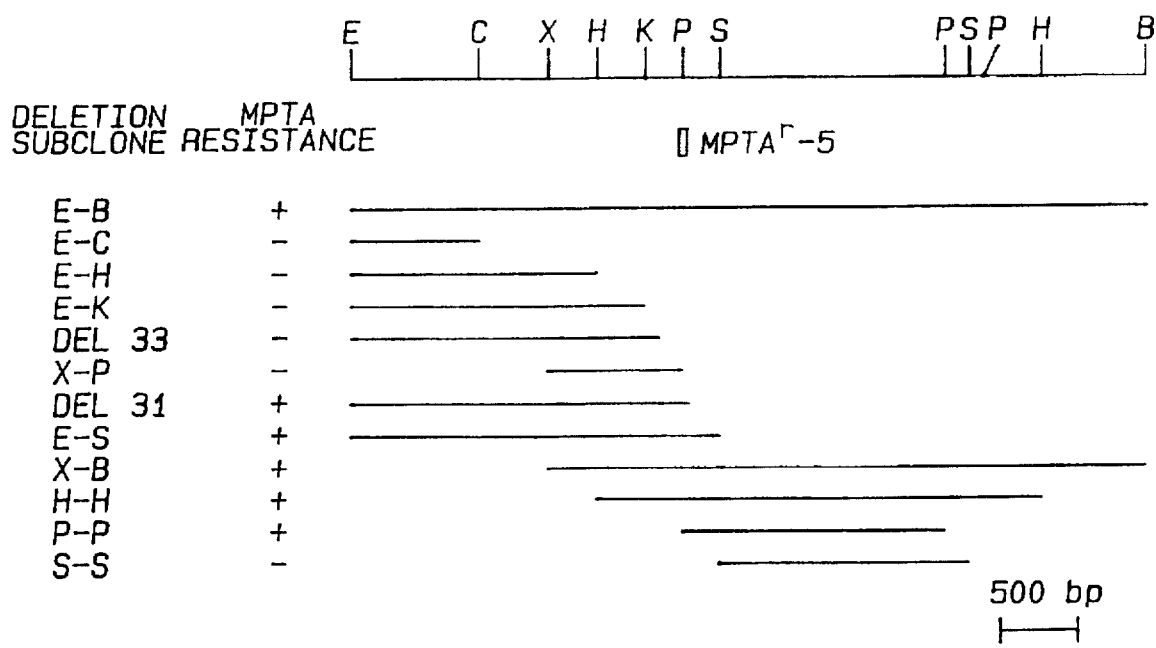
FIG. 4 is a diagram representing a map showing that lycopene cyclase activity maps to a region that includes the MPTA resistance lesion(s), abbreviations are as in FIG. 3.
Figure 5:
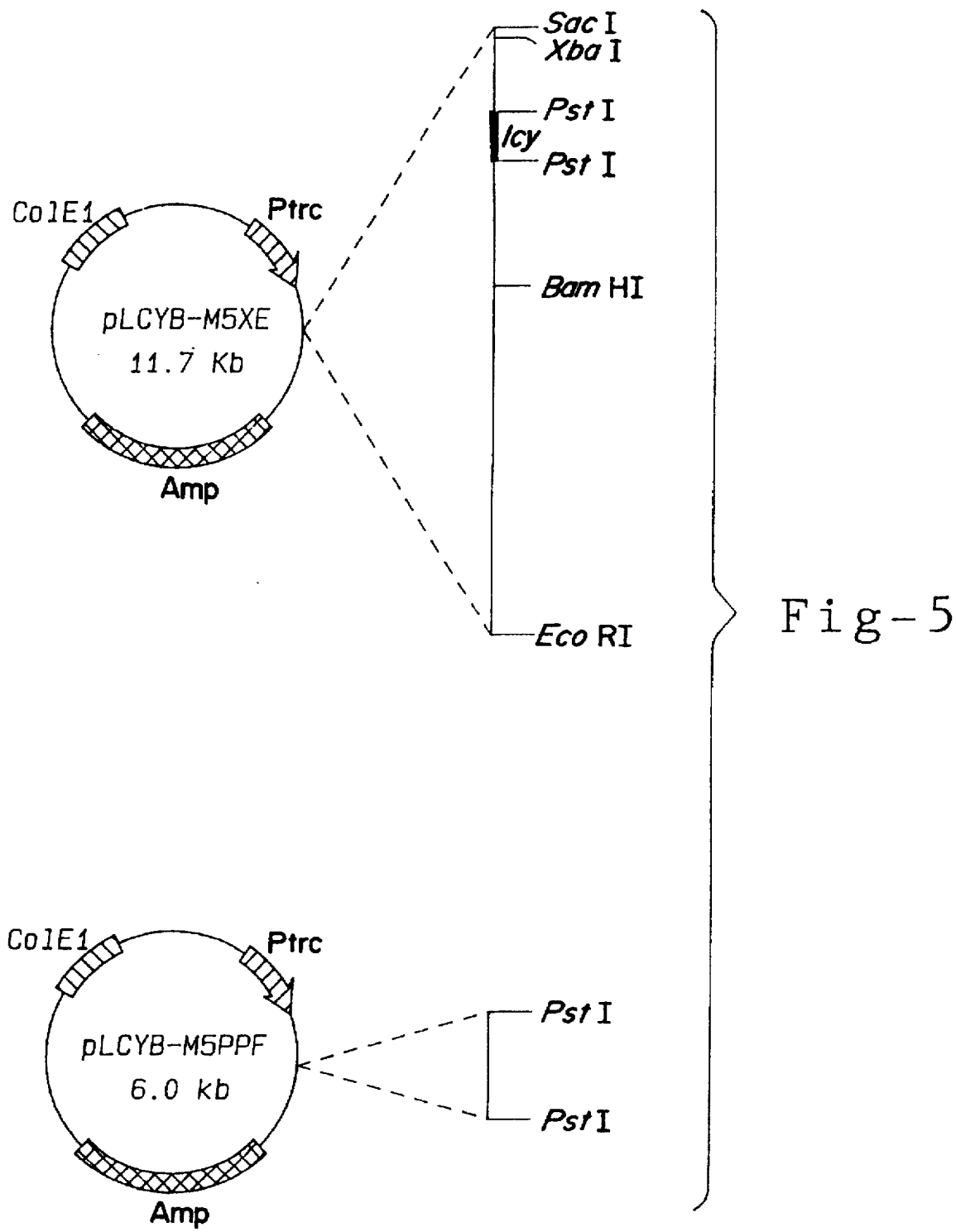
FIG. 5 is a diagram of the construction of plasmids pLCYB-M5XE and pLCYB-M5PPF wherein the putative localization of the lcy (crtL) gene in mutant number 5 is based on expression experiments (see FIG. 4)
Figure 6:
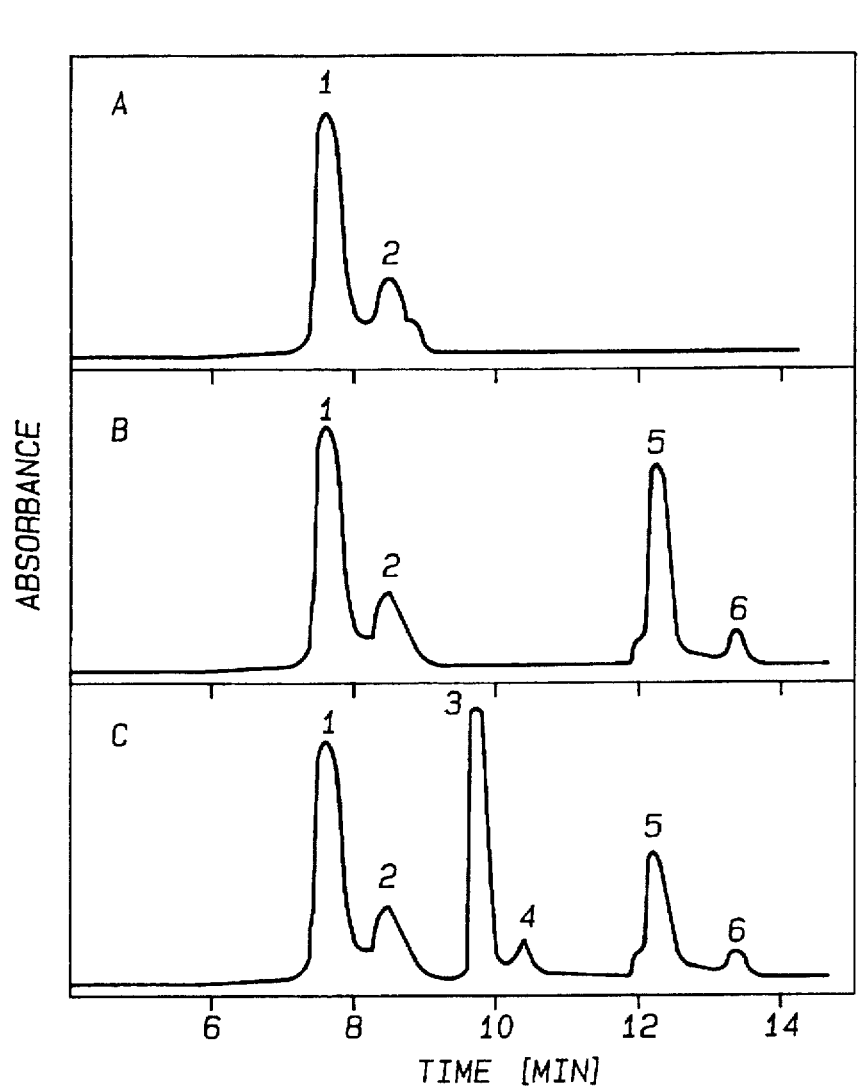
FIG. 6 is a graph presenting the HPLC analysis of carotenoid pigments extracted from cells of a lycopene-accumulating strain of *E. coli* (panel A), a lycopene-accumulating strain of *E. coli* containing pLCYB-M5XE (panel B), a lycopene-accumulating strain of *E. coli* containing pLCYB-M5XE in the presence of MPTA (panel C) wherein the effect of treatment of the *E. coli* cells with 100 mM MPTA is shown, and the absorbance spectra of peaks 1, 3 and 5 are shown in the lower panel {(- - -) peak 1 is lycopene; (_____) peak 3 is γ-carotene; ( . . . ) peak 5 is β-carotene}.
Figure 6:
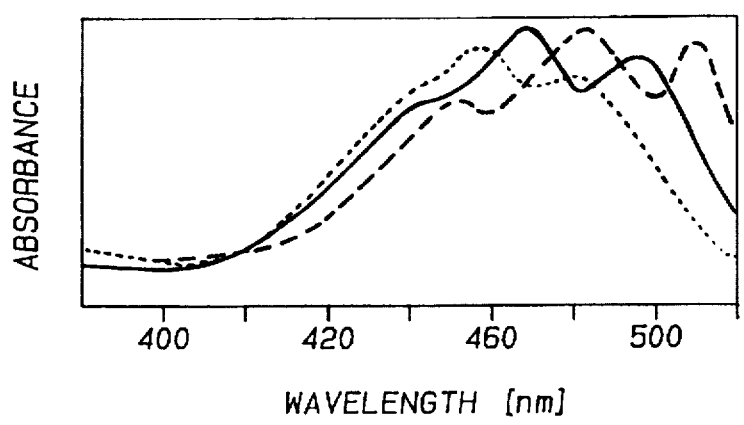

The plasmid pLCYB-M5XE, which contains a 7.2 kb genomic insert (FIG. 5), was introduced into cells of *E. coli* which accumulated lycopene. In the presence or absence of IPTG, colonies and cultures of cells also containing pLCYB-M5XE were yellow in color and contained β-carotene in addition to lycopene as revealed by HPLC analysis (FIG. 6). A number of other genomic fragments which contained the mutation, the smallest of which was a 1.5 kb PstI-PstI fragment in the vector pTrcHisB (plasmid pLCYB-M5PPF), gave results similar to those shown in FIG. 6 (see also FIG. 4). Enzymatic activity was observed with the 1.5 kB PstI fragment cloned in all three frames of the pTrcHis vector and was independent of IPTG induction. Activity was not observed if the fragment was cloned in the reverse orientation. It was concluded that binding of *E. coli* DNA polymerase to the promoter of the vector facilitates recognition and utilization of a cyanobacterial promoter and production of the authentic cyanobacterial enzyme rather than a fusion protein. A truncated version of pLCYB-M5PPF, lacking only the 0.2 kb PstI-SalI portion containing the MPTA-resistant mutation (pLYCB-M5SP), did not sustain lycopene cyclase activity in *E. coli* cells.

DNA sequence analysis revealed a single open reading frame coincident with the mapped location of lycopene cyclase activity (FIG. 7). Applicants concluded that this putative gene, designated as lcy, encodes the enzyme lycopene cyclase, and that this single gene product is sufficient to catalyze both cyclization steps required to produce β-carotene from lycopene.

4. Lycopene Cyclase is the Target Site for MPTA inhibition.

Suspension cultures of transformed *E. coli* cells were grown in the presence of 100 μM MPTA in order to examine the interaction between the herbicide and lycopene cyclization activity. HPLC analysis of the carotenoids, shown in FIG. 6, indicated that these cells accumulated significant amounts of monocyclic γ-carotene, in addition to lycopene and β-carotene, whereas no γ-carotene was detected in the absence of MPTA. Applicants concluded that MPTA acts directly as an inhibitor of lycopene cyclase.

5. Identification of a mutation for MPTA resistance (FIG. 7).

DNA sequence analysis in the region conferring lycopene cyclase activity (FIG. 4) revealed a single open reading frame, lcy. This open reading frame is of a size to encode a protein of 411 amino acids with a predicted molecular weight of 46,093 g/mol (SEQ ID No:2).

Mutant 5 differs from the wild-type at a single position (position 1925 of SEQ ID No:1), 104 bp upstream of the expected initiation codon of the gene in the promoter region of lcy that provides resistance to MPTA. The mutation does not alter the amino acid sequence of the protein encoded by open reading frame 2 (ORF2). The change of a C in the wild-type to a T in M'-5 produces a 6 base sequence (TACAAT) closer to the consensus for the −10 or Pribnow box of the *E. coli* promoter region (TATAAT). This T residue in position six of the *E. coli* consensus promoter is highly conserved (96%) while that in the third position is the least conserved base (44%) (Hawley et al, 1983). The mutation to a T in M'-5 is expected to facilitate DNA strand separation and thereby enhance mRNA production. Overproduction of this message and, consequently, of the enzyme itself, is the most likely explanation for the greatly enhanced MPTA-resistance of mutant 5. This mutant would be expected to be resistant to any other herbicides that act by interfering with lycopene cyclase activity.

Searches of GenBank and SwissProt DNA and protein sequence data banks unearthed no genes or proteins with appreciable sequence similarity to lcy. The only resemblance of the predicted amino acid sequence of the protein encoded by lcy to other known or reported proteins occurs at the amino terminus of LCY. A nucleotide-binding motif (SEQ ID No:3) is present here in LCY and indicates that this enzyme binds and utilizes cofactor FAD (FIG. 8).

6. Isolation and sequences of the crtL cDNA in tobacco (SEQ ID No:4) and tomato (SEQ ID No:5).

The tobacco cDNA sequence (SEQ ID No:4) was obtained by screening a leaf cDNA library of *Nicotiana tabacum* (cv. xanthii) using the crtL gene (for lycopene cyclase) from Synechococcus PCC7942 as a molecular probe. The sequence has been deposited in EMBL/Genbank and has the accession number X81787. The cDNA library is a standard library that was constructed in phage lambda and screened using procedures as generally described in Sambrook et al., *Molecular Cloning: A Laboratory Manual*, Cold Springs Harbor Laboratory, New York (1992) and in Ausubel et al., *Current Protocols in Molecular Biology*, John Wiley and Sons, Baltimore, Md. (1989). This cDNA sequence (SEQ ID No:4) when carried in a plasmid vector such as described for the crtL gene from Synechococcus PCC7942, in any of two orientations, can be expressed in *E. coli* cells, produces an active lycopene cyclase enzyme. Its biochemical characteristics are identical to the cyanobacterial enzyme, as described by Cunningham, et al (1993, 1994) and herein above.

The tomato cDNA sequence (SEQ ID No:5) was obtained by screening a leaf cDNA library of Lycopersicon asculentum (cv FV36) using the crtL gene (for lycopene cyclase) from Synechococcus PCC7942 as a molecular probe. The cDNA library is a standard library that was constructed in phage lambda and screened using procedures as generally described in Sambrook et al., *Molecular Cloning: A Laboratory Manual*, Cold Springs Harbor Laboratory, New York (1992) and in Ausubel et al., *Current Protocols in Molecular Biology*, John Wiley and Sons, Baltimore, Md. (1989).

This cDNA sequence (SEQ ID No:5) when carried in a plasmid vector such as described for the crtL gene from Synechococcus PCC7942, in any of two orientations, can be expressed in *E. coli* cells, produces an active lycopene cyclase enzyme. Its biochemical characteristics are identical to the cyanobacterial enzyme, as described by Cunningham, et al (1993, 1994) and herein above.

Throughout this application various publications are referenced. Full citations for the referenced publications not cited herein above are listed below. The disclosures of these publications in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope

REFERENCES CITED

Armstrong (1994) *J. Bacteriology,* 176:4795–4802 Armstrong et al. (1989) *Mol. Gen. Genet.,* 216:254:268 Bartley et al. (1991) *Proc. Natl. Acad. Sci. USA,* 88:6532–6536 Bartley et al. (1992) *J. Biol. Chem.,* 267:5036–5039 Beaversdorf et al. (1980) *Crop Science,* 20:289 Beyer et al. (1980) *Planta,* 150:435–438 Beyer (1989) in: *Physiology, Biochemistry and Genetics of Nongreen Plastids,* American Society of Plant Physiology, pp. 157–170 Bird et al. (1991) *Biotechnology,* 9:635–639 Bramley, (1985) *Adv. Lipid Res.,* 21:243–279 Bramley, et al. (1992) *Plant J.,* 2:343–349 Britton (1988) *Plant Pigments* (Academic Press, NY) pp. 133–180 Bucholtz et al. (1977) *Chem. Biol. Interactions,* 17:359–362 Camara et al. (1982) *.Physiol. Veg.* 20:757–773 Chamovitz (1990) *Z. Naturforsch,* 45c:482–486 Chamovitz et al. (1991) *Plant Mol. Biol.,* 16:967–974 Chamovitz et al. (1992) *FEBS Lett.,* 296:305–310 Cunningham (1985) (Ph.D. Thesis, Brandeis Univ.) Chap. 4, pp. 5–17 Cunningham et al. (1993) *FEBS Lett.,* 328:130–138 Cunningham et al. (1994) *Plant Cell* 6:1107–1121 Del Sal et al. (1988) *Nucleic Acids Res.,* 16:9878 Demmig-Adams et al. (1992) *Ann. Rev. Plant Physiol. Plant Mol. Biol.,* 43:599–626 (1992) Dogbo et al. (1988) *Proc. Natl. Acad. Sci. USA,* 85:7054–7058 Feinberg et al. (1983) *Anal. Biochem.,* 132:6–13 Fosket et al. (1983) *Plant Sci. Lett.,* 30:165–175 Gilboa et al. (1986) *BioTechniques* 4(6):504–512, 1986. Golden (1988) *Methods Enzymol.,* 167:714–727 Gray et al. (1994) *Plant Cell Environ.,* 17:557–571 Hali et al. (1993) *Plant J.,* 3:121–129 Hall et al. (1993) *Plan J.,* 3:121–129 Hawley et al. (1983) *Nucleic Acids Res.* 11:2244 Hirschberg et al. (1987) *Z. Naturforsch.,* 42c:102–112 Hsu et al. (1972) *Phytochemistry,* 11:2985–2990 Hugueney et al. (1992) *Eur. J. Biochem.,* 209:399–407 Hundle et al. (1991) *Photochem Photobiol.,* 54:89093 Hundle et al. (1993) *FEBS Lett.,* 315:329–334 Koyama (1991) *Photochem. Photobiol B* 9:265–280 Linden et al. (1991) *Z. Naturforsch.,* 46c:1045–1051 Linden et al. (1993) *FEMS Microbiol. Lett.,* 106:99–104 Mathews-Roth et al. (1991) *Oncology,* 48:177–179 Misawa et al. (1990) *J. Bacteriol.,* 172:6704–6712 Misawa et al. (1991) *Appl. Environ. Microbiol.,* 57:1847–1849 Misawa et al. (1994a) *Plant J.,* 6:481–489 Misawa et al. (1994b) *J. Biochem,* Tokyo, 116:980–985 Palozza et al. (1992) *Methods Enzymol.,* 213:403–420 Pecker et al. (1992) *Proc. Natl. Acad. Sci. USA,* 89:4962–4966 Pecker et al. (1993) *Research in Photosynthesis,* Vol III (Kluwer Academic Publishers, Dordrectht) pp. 11–18 Ray et al. (1987) *Nucleic Acids Res.,* 15:10587–10588 Rock et al. (1991) *Proc. Natl. Acad. Sci. USA,* 88:7496–7499 Sambrook et al. (1989) *Molecular Cloning: A Lab. Manual,* 2nd, Cold Spring Lab. Press, Cold Spring Harbor, pp 316–317, 326–328 Sandmann et al. (1989a) *Z. Naturforsch.,* 44c:787–790 Sandmann et al. (1989b) in *Target sites of herbicide action* (CRC Press, Florida) pp. 25–44 Sandmann et al. (1990) *FEMS Microbiol. Lett.,* 71:77–82 Schnurr et al (1991) *FEMS Microbiol Lett.,* 78:157–162 Siefermann-Harms (1987) *Physiol. Plant.,* 69:265–280, 561–568 Williams (1988) *Methods Enzymol.,* 167:766–778 Yokoyama et al. (1982) in *Carotenoid Chem. and Biochem.* (Pergamon Press, Oxford) pp. 371–385 Zeevaart et al. (1988) *Ann. Rev. Plant Physiol. Plant Mol. Biol.,* 39:439–473 of the appended claims, the invention may be practiced otherwise than as specifically described.

We claim:

1. A purified, isolated and cloned DNA, designated lcy or crtL, which encodes a lycopene cyclase in oxygenic photosynthetic organisms.

2. A DNA sequence as set forth in claim 1 selected from the group consisting of SEQ ID No:1 (bp2029-3261), SEQ ID No:4 and SEQ ID No:5.

3. An *E. coli* transformed with the DNA sequence for lycopene cyclase as set forth in claim 1.

4. A vector which comprises the DNA of claim 1.

5. A host cell, wherein the host cell is selected from the group consisting of photosynthetic eucaryotic and procaryotic cells, which can be transformed with the vector of claim 4.

6. The host cell of claim 5 wherein it is E. coli.

7. The host cell of claim 5 wherein it is a cyanobacteria.

8. The host cell of claim 7 wherein it is selected from the group consisting of Synechococcus PCC7942 and Synechocystis PCC6803.

9. The host cell of claim 5 wherein it is an alga.

10. The host cell of claim 5 wherein it is a plant cell.

11. A purified, isolated and cloned DNA sequence comprising a nucleotide sequence for lcy which encodes a lycopene cyclase (LCY) polypeptide and at least one flanking DNA sequence.

12. A purified, isolated and cloned DNA sequence as set forth in claim 11 wherein the flanking DNA sequence is a promoter.

13. The DNA sequence of claim 11 wherein the nucleotide sequence for lcy is selected from the group consisting of SEQ ID No:1 (bp2029-3261), SEQ ID No:4 and SEQ ID No:5.

14. A vector which comprises the DNA of claim 11.

15. A host cell, wherein the host cell is selected from the group consisting of photosynthetic eucaryotic and procaryotic cells which can be transformed with the vector of claim 14.

16. The host cell of claim wherein it is *E. coli*.

17. The host cell of claim 15 wherein it is a cyanobacteria.

18. The host cell of claim 17, wherein it is selected from the group consisting of Synechococcus PCC7942 and Synechocystis PCC6803.

19. The host cell of claim wherein it is an alga.

20. The host cell of claim wherein it is a plant cell.

21. A transgenic procaryotic or photosynthetic eucaryotic organism wherein the lcy DNA sequence is incorporated into the genomic DNA thereby producing lycopene cyclase and β-carotene.

22. A process of modifying carotenoid biosynthesis, content, composition or amount relative to an untransformed bacteria, algae, or plant cell by preparing vectors of a DNA sequence consisting of a purified, isolated and cloned DNA sequence comprising a nucleotide sequence for lcy which encodes a lycopene cyclase (LCY) polypeptide and at least one flanking DNA sequence; and inserting said vectors in the cells of bacteria, algae and plants thereby forming transgenic organisms.

23. The process of claim 22 wherein the vector consists of the lcy DNA sequence and a promoter.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
      ( A ) LENGTH: 4928 base pairs
      ( B ) TYPE: nucleic acid
      ( C ) STRANDEDNESS: single
      ( D ) TOPOLOGY: linear ( i i ) MOLECULE TYPE: DNA (genomic)

( i x ) FEATURE:
      ( A ) NAME/KEY: CDS
      ( B ) LOCATION: 2029..3261

( x i ) SEQUENCE DESCRIPTION: SEQ ID NO:1:

```
GAATTCTGCA  AAGCCTCTTG  ATTCGTTGGT  GCCTTGAATT  AGTTTTAGAA  CTGCCTGAGG        60

AAGCGCAAAT  CGCTGGCGTA  GAGGCGGCGA  ATATCGTCCA  TGCCGTGCAG  CACCATCGCA       120

AAACGCTCCA  CCCCAAAACC  GGCTGCAAAG  CCGCTGTAGG  TTTCTGGGTC  GCAGCCCACG       180

GCTTTGAGAA  CATTGGGATC  GACCATGCCG  CAGCCCAAGA  CCTCTAGCCA  TTTCCCTTGC       240

CAGAGCACAT  CGACTTCTGC  CGAAGGTTCC  GTGAAGGGGA  AGAAGCTGGC  ACGGAAGCGG       300

ATCGGTAGGT  CGCCGAATAG  CGCCTGAATC  AGGGTTTTGA  CGGTGCCTTT  CAGGTCAGTG       360

AAAGTCAAGC  CTTCATCAAC  GGCGAGTAGT  TCCACTTGGT  GGAAGACGGC  CGAATGAGTC       420

GCATCAACGG  CATCGCGCCG  GTAAACGCGT  CCGGGCGCGA  CGACTCGAAT  CGGCGGCTCC       480
```

-continued

```
TGCTCTTCCA TGTGGCGAAT CTGCACGGAC GATGTGTGAG TGCGCAGCAG ATTGCCGTCA        540
GTGAGGTAGA AGGTGTCCTG CATGTCCCGC GCTGGGTGGT CGGCGGGCAT GTTTAGGGCT        600
TCGAAGTTGT AGTAATCCGA CTCCATTTCT GGCCCCTCAG CGACTTGATA GCCAAGGCCA        660
ACGAGGATGT CGAGAATGCG ATCGATCGTG CTTTGCAGCG GGTGAAGGTG TCCCTGGGGA        720
CGATACTGCC CTGGCATGGT GACATCGATT GCTTCTGCAA TCAGTCGCGC TTCTAGTTCT        780
GCTTTGCCGA GGGCTTCACG CCGTTCATCG AGGTCAGTAC TAATGCGGGC TTTAACGGTG        840
TTTGCCAACC CACCAATGCG AGGGCGATCG CTGGCATCCA GTTTGCCCAT CGCACCCAAA        900
ATGGCTGAAA GCTCCCCTTT TTTGCCCAAA AAGGCGATGC GCAGTTGCTC CAAGGCTTCC        960
CGATCGCTCG CTGTGGCGAT CGCTTCCAGA GCACGGGTTT GCAGAGCTTC GAGTTGAGCC       1020
TCAAGCTCGC TGAGCTGACT GAGCATAGGA TTCAAGCAAA AGGGGCGGGG GAGCCATCAA       1080
AGTCCAGATT ACCAGCCGTG CGATCGCGCC GGTGTGCGGG TCTAGACCGG TTATGCTCCC       1140
CGAATGCCGT TAGGGTTAAT GGGCAGACCC TGCAATTCGG CATGCGACTT CTGATCAGCA       1200
ACGACGATGG CGTTTTCGCC CTCGGTATCC AAACCCTCGC CAACCGTCTC GTTCAGGCTG       1260
GCCATGAGGT CACGGTTGTC TGTCCCGATC GCGAGCGATC GGCCACCGGC CACGGCCTGA       1320
CGTTGCATAA ACCCATCCGC GCCGAACGGA TCGAAGGGCT GTTTGATCCG GCAGTACAGG       1380
TCTGGGCTTG CTCTGGGACG CCTTCGGACT GCGTCAAGCT TGCCCTTGGC ACACTGCTGC       1440
CAGAACTGCC CGATTTTGTG CTCTCGGGCA TCAATCACGG CCCCAATCTG GAACGGACG       1500
TGCTCTACTC CGGCACCGTC TCAGCAGCGA TGGAGGGCGT GATTGAAGGT ATCCCCAGCA       1560
TTGCCCTGAG CTTGGCCAGT TTTACAGCGC GGGACTTTGA CCAGCGGCT GAGATTGCTG        1620
TGGAATTACT GGAGCGCCTG CCGCACCCCA GTTCGCCCAA GGTGCTGCTC AGCGTCAACA       1680
TTCCGCCGGT ACCGAAGGAG GAAATCGCTG GCATTCGCCT GACCCGCCAA GGCGTCCGAC       1740
GCTACGTCGA TCTGTTTGAC CAGCGGGTCG ATCCACGCGG TAAGCCCTAT TTCTGGCTAG       1800
CCGGTGAGGT GGTGGAAGAA AGTGAACCAC AGGAACCGGC TGATAGCCAC TGGTGCGATG       1860
TCGATGCGAT CCGCCGCAAC TACGTGACGG TAACGCCGCT GCAGTACGAC CTGACGCACT       1920
ACAATAGCCT CAGTCAGCTC GATCACCTCA GCCGCTAGGG GCGATTGCCC CCTCAGGGCT       1980
AGGATCGCAA GCGGTGATAG TAGCGCAAGC AACAGGGAGA GCGATCGC GTG TTC GAT       2037
                                                      Val Phe Asp
                                                        1
GCC TTA GTG ATC GGG TCG GGG CCA GCC GGA CTG GCG ATC GCG GCA GAG        2085
Ala Leu Val Ile Gly Ser Gly Pro Ala Gly Leu Ala Ile Ala Ala Glu
      5                  10                  15
CTG GCA CAG CGC GGC TTG AAA GTC CAA GGA CTA TCC CCC GTC GAC CCA        2133
Leu Ala Gln Arg Gly Leu Lys Val Gln Gly Leu Ser Pro Val Asp Pro
 20                  25                  30                  35
TTC CAT CCT TGG GAA AAT ACC TAC GGC ATC TGG GGA CCC GAG CTG GAT        2181
Phe His Pro Trp Glu Asn Thr Tyr Gly Ile Trp Gly Pro Glu Leu Asp
             40                  45                  50
AGT CTT GGC CTC GAG CAT CTC TTT GGG CAT CGC TGG TCG AAC TGC GTT        2229
Ser Leu Gly Leu Glu His Leu Phe Gly His Arg Trp Ser Asn Cys Val
         55                  60                  65
AGC TAC TTC GGT GAG GCG CCG GTT CAG CAC CAA TAC AAC TAC GGG CTG        2277
Ser Tyr Phe Gly Glu Ala Pro Val Gln His Gln Tyr Asn Tyr Gly Leu
     70                  75                  80
TTT GAT CGC GCC CAA CTA CAA CAG CAC TGG TTG CGG CAA TGT GAG CAA        2325
Phe Asp Arg Ala Gln Leu Gln Gln His Trp Leu Arg Gln Cys Glu Gln
 85                  90                  95
GGC GGC CTG CAA TGG CAA CTC GGC AAA GCA GCT GCG ATC GCC CAT GAC        2373
```

```
Gly Gly Leu Gln Trp Gln Leu Gly Lys Ala Ala Ala Ile Ala His Asp
100             105                 110                 115

TCC CAC CAT TCC TGC GTT ACG ACA GCA GCA GGG CAG GAG TTA CAG GCG        2421
Ser His His Ser Cys Val Thr Thr Ala Ala Gly Gln Glu Leu Gln Ala
                120                 125                 130

CGG CTG GTT GTC GAT ACG ACT GGG CAC CAA GCG GCT TTT ATC CAG CGA        2469
Arg Leu Val Val Asp Thr Thr Gly His Gln Ala Ala Phe Ile Gln Arg
                135                 140                 145

CCT CAT TCA GAC GCG ATC GCC TAC CAA GCG GCC TAC GGC ATC ATT GGC        2517
Pro His Ser Asp Ala Ile Ala Tyr Gln Ala Ala Tyr Gly Ile Ile Gly
                150                 155                 160

CAG TTT TCG CAG CCG CCG ATC GAG CCC CAT CAG TTT GTG CTG ATG GAC        2565
Gln Phe Ser Gln Pro Pro Ile Glu Pro His Gln Phe Val Leu Met Asp
        165                 170                 175

TAC CGC AGC GAC CAT CTC TCA CCT GAA GAA CGC CAA CTG CCA CCG ACC        2613
Tyr Arg Ser Asp His Leu Ser Pro Glu Glu Arg Gln Leu Pro Pro Thr
180                 185                 190                 195

TTT CTC TAC GCG ATG GAT CTC GGG AAC GAC GTC TAC TTT GTA GAG GAA        2661
Phe Leu Tyr Ala Met Asp Leu Gly Asn Asp Val Tyr Phe Val Glu Glu
                200                 205                 210

ACA TCG CTG GCG GCT TGC CCG GCT ATT CCC TAC GAT CGC CTC AAA CAA        2709
Thr Ser Leu Ala Ala Cys Pro Ala Ile Pro Tyr Asp Arg Leu Lys Gln
                215                 220                 225

CGG CTC TAT CAA CGC TTA GCC ACT CGC GGT GTG ACG GTG CAA GTG ATT        2757
Arg Leu Tyr Gln Arg Leu Ala Thr Arg Gly Val Thr Val Gln Val Ile
                230                 235                 240

CAG CAC GAG GAA TAT TGC CTG TTT CCG ATG AAT TTG CCG CTG CCC GAT        2805
Gln His Glu Glu Tyr Cys Leu Phe Pro Met Asn Leu Pro Leu Pro Asp
        245                 250                 255

CTC ACT CAG TCA GTG GTT GGC TTT GGG GGG GCG GCC AGT ATG GTG CAT        2853
Leu Thr Gln Ser Val Val Gly Phe Gly Gly Ala Ala Ser Met Val His
260                 265                 270                 275

CCC GCT TCG GGC TAC ATG GTC GGG GCG CTA CTG CGG CGC GCT CCT GAT        2901
Pro Ala Ser Gly Tyr Met Val Gly Ala Leu Leu Arg Arg Ala Pro Asp
                280                 285                 290

CTG GCG AAT GCG ATC GCG GCT GGA CTG AAT GCC AGT TCC AGT CTG ACC        2949
Leu Ala Asn Ala Ile Ala Ala Gly Leu Asn Ala Ser Ser Ser Leu Thr
                295                 300                 305

ACG GCA GAA CTT GCT ACC CAA GCC TGG CGA GGA CTC TGG CCA ACC GAA        2997
Thr Ala Glu Leu Ala Thr Gln Ala Trp Arg Gly Leu Trp Pro Thr Glu
        310                 315                 320

AAA ATT CGC AAG CAC TAC ATC TAC CAA TTC GGC CTC GAA AAG CTG ATG        3045
Lys Ile Arg Lys His Tyr Ile Tyr Gln Phe Gly Leu Glu Lys Leu Met
        325                 330                 335

CGC TTT TCC GAA GCC CAG CTC AAT CAT CAC TTC CAG ACC TTC TTT GGC        3093
Arg Phe Ser Glu Ala Gln Leu Asn His His Phe Gln Thr Phe Phe Gly
340                 345                 350                 355

CTG CCG AAG GAG CAG TGG TAC GGC TTT TTG ACC AAT ACG CTG TCG CTA        3141
Leu Pro Lys Glu Gln Trp Tyr Gly Phe Leu Thr Asn Thr Leu Ser Leu
                360                 365                 370

CCG GAG CTG ATT CAA GCG ATG CTC AGA TTA TTT GCC CAA GCG CCG AAT        3189
Pro Glu Leu Ile Gln Ala Met Leu Arg Leu Phe Ala Gln Ala Pro Asn
                375                 380                 385

GAT GTG CGC TGG GGT CTG ATG GAA CAA CAA GGT CGC GAA TTA CAA CTC        3237
Asp Val Arg Trp Gly Leu Met Glu Gln Gln Gly Arg Glu Leu Gln Leu
                390                 395                 400

TTT TGG CAA GCG ATC GCG GCC CGC TAGCTGCTAA AAACTAGCCG CCCTTGCCAA       3291
Phe Trp Gln Ala Ile Ala Ala Arg
        405                 410

TATCCCGTAA AGTTTTTGAA GCGCTGCTGC ACTTGTTACA GAACCCTAGC GAGCACTTGT      3351
```

| | | | | | |
|---|---|---|---|---|---|
| CCTGGTTCCA | CTTGAGGATC | GATTCCCCCG | AGTAATGGCT | TCCGAGAACT | ACCTCAACCA | 3411
| TCCCACCTTC | GGATTGCTCT | ACCAAATCTG | CAGCTTTGGG | GACAGCAAAG | AACTCTTCGC | 3471
| CACTCTTTAT | GCTCAGCGCC | TCTTTTTTCT | CGTAGCCTTT | GATGCTCGGG | GAACCCGCTT | 3531
| TGAGCCAATC | GGTCGTAATG | AAGCGCGGAT | GTTGGTCGAC | AACCGTCTGC | GCCAGCTGCG | 3591
| CCGAGATGCC | AGTCTGCAGG | AATACAACCA | GCTGCAGCAA | GTCTTCAAAC | AAACCTTTCT | 3651
| GTAGCCAGCT | AGGGAGTCAG | AGGCAGGCAT | GGCCCAAATT | GCCGAGCGGT | TGGCCAGTCT | 3711
| CCGATCGCAA | CTGCCTCCCA | GCGTTCAGCT | GATTGCTGTC | AGCAAGAACC | ATCCCGCTGC | 3771
| TGCCATCCGA | GAAGCCTATG | CAGCAGGTCA | GCGGCACTTT | GGCGAAAATC | GGGTCCAAGA | 3831
| AGCGATCGCT | AAGCAAGCGG | AACTGACGGA | TCTGCCCGAT | TTGACTTGGC | ATCTGCTGGG | 3891
| AAAACTGCAG | AGCAATAAAG | CCCGGAAAGC | TGTCGAGCAT | TTCGACTGGA | TTCATTCAGT | 3951
| TGATAGCTGG | GCCTTGGCTG | AACGACTCGA | TCGCATTGCG | GGAGAGTTGG | GGCGATCGCC | 4011
| CAAGCTTTGC | CTCCAGGTGA | AGCTCCTGCC | TGACCCCAAC | AAAGCGGGCT | GGGACCCTGC | 4071
| TGATTTGCGG | GCTGAGTTAC | CGCAGCTCAG | TCAACTCCAA | CAGGTACAAA | TCCGCGGCTT | 4131
| GATGGTGATT | GCGCCCCTCG | GACTCACCGC | CGCTGAGACT | CAGGCTCTGT | TTGCGCAGGC | 4191
| TCGCACCTTC | GCCGCCGAGT | TGCAGCAGCA | GGCTCCGCAG | CTACGGCTCA | CGGAACTCTC | 4251
| GATGGGCATG | TCGAGTGACT | GGCCTTTGGC | TGTGGCGGAA | GGGGCAACTT | GGATTCGAGT | 4311
| CGGAACCCAG | TTATTTGGGC | CGCGATCGCT | GTAATCTTGG | CCATAGTTAA | CAAACCTTTA | 4371
| CGTCTTAGAA | CTGGCCTAGC | AATTGCCATT | TCAGGTGCTT | TAAGTGGCTT | TCCTTAAAAA | 4431
| AAGCTGAGAT | TTGTTCGGTA | AAACCAGTCG | AAATCTTGCC | GTTTGTGCTA | TTACTACTGC | 4491
| GTCTCCATCG | ACCTAAGCAG | TGCCCTGCGC | TCTCGCTAGT | GGTCAGCGGA | AAAGTGTGGT | 4551
| GTCGTTGCCC | TTGGAGGAAC | TGATCGTGTC | TTTTGTGAAC | CGGATCCGCG | ATATCGTCGG | 4611
| TCTCAATGAG | TCGCTGGACT | ACGACGAAGA | GTACGAAACC | TACGATGTGG | CAGCGGACTC | 4671
| TTACAACGGT | TATAACGACG | CTGCCGAAAC | CAGTTCCCGC | CGGAGACAGC | GCAACCATAC | 4731
| GCCGACTGCC | AGTATTGAAC | CGGTTAGTAC | GGCCAGCAAT | GTGATTGGCT | TGCCGGTCTG | 4791
| AGCAGCAGCT | CAGAAGTGGT | GGTAATGGAA | CCCGCTCTTT | CGAAGAAATG | CCCAGGCCAT | 4851
| TCAGGCTTTG | ACGCGAACGC | AAGACGATCG | TGCTGAACCT | GACGATGATG | GAGCTGACAG | 4911
| CACAGGCGCG | TCGATTT | | | | | 4928

( 2 ) INFORMATION FOR SEQ ID NO:2:

( i ) SEQUENCE CHARACTERISTICS:
        ( A ) LENGTH: 411 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Val | Phe | Asp | Ala | Leu | Val | Ile | Gly | Ser | Gly | Pro | Ala | Gly | Leu | Ala | Ile |
|---|---|---|---|---|---|---|---|---|---|---|---|---|---|---|---|
| 1 | | | | 5 | | | | | 10 | | | | | 15 | |

| Ala | Ala | Glu | Leu | Ala | Gln | Arg | Gly | Leu | Lys | Val | Gln | Gly | Leu | Ser | Pro |
|---|---|---|---|---|---|---|---|---|---|---|---|---|---|---|---|
| | | | 20 | | | | | 25 | | | | | 30 | | |

| Val | Asp | Pro | Phe | His | Pro | Trp | Glu | Asn | Thr | Tyr | Gly | Ile | Trp | Gly | Pro |
|---|---|---|---|---|---|---|---|---|---|---|---|---|---|---|---|
| | | 35 | | | | | 40 | | | | | 45 | | | |

| Glu | Leu | Asp | Ser | Leu | Gly | Leu | Glu | His | Leu | Phe | Gly | His | Arg | Trp | Ser |
|---|---|---|---|---|---|---|---|---|---|---|---|---|---|---|---|
| | 50 | | | | | 55 | | | | | 60 | | | | |

| Asn | Cys | Val | Ser | Tyr | Phe | Gly | Glu | Ala | Pro | Val | Gln | His | Gln | Tyr | Asn |

```
     65                   70                   75                   80
Tyr  Gly  Leu  Phe  Asp  Arg  Ala  Gln  Leu  Gln  Gln  His  Trp  Leu  Arg  Gln
                    85                        90                        95

Cys  Glu  Gln  Gly  Gly  Leu  Gln  Trp  Gln  Leu  Gly  Lys  Ala  Ala  Ala  Ile
                    100                       105                       110

Ala  His  Asp  Ser  His  His  Ser  Cys  Val  Thr  Thr  Ala  Ala  Gly  Gln  Glu
                    115                       120                       125

Leu  Gln  Ala  Arg  Leu  Val  Val  Asp  Thr  Thr  Gly  His  Gln  Ala  Ala  Phe
          130                       135                       140

Ile  Gln  Arg  Pro  His  Ser  Asp  Ala  Ile  Ala  Tyr  Gln  Ala  Ala  Tyr  Gly
145                           150                       155                       160

Ile  Ile  Gly  Gln  Phe  Ser  Gln  Pro  Pro  Ile  Glu  Pro  His  Gln  Phe  Val
                    165                       170                       175

Leu  Met  Asp  Tyr  Arg  Ser  Asp  His  Leu  Ser  Pro  Glu  Glu  Arg  Gln  Leu
                    180                       185                       190

Pro  Pro  Thr  Phe  Leu  Tyr  Ala  Met  Asp  Leu  Gly  Asn  Asp  Val  Tyr  Phe
               195                       200                       205

Val  Glu  Glu  Thr  Ser  Leu  Ala  Ala  Cys  Pro  Ala  Ile  Pro  Tyr  Asp  Arg
     210                       215                       220

Leu  Lys  Gln  Arg  Leu  Tyr  Gln  Arg  Leu  Ala  Thr  Arg  Gly  Val  Thr  Val
225                      230                       235                       240

Gln  Val  Ile  Gln  His  Glu  Glu  Tyr  Cys  Leu  Phe  Pro  Met  Asn  Leu  Pro
               245                       250                       255

Leu  Pro  Asp  Leu  Thr  Gln  Ser  Val  Val  Gly  Phe  Gly  Gly  Ala  Ala  Ser
               260                       265                       270

Met  Val  His  Pro  Ala  Ser  Gly  Tyr  Met  Val  Gly  Ala  Leu  Leu  Arg  Arg
          275                       280                       285

Ala  Pro  Asp  Leu  Ala  Asn  Ala  Ile  Ala  Ala  Gly  Leu  Asn  Ala  Ser  Ser
     290                       295                       300

Ser  Leu  Thr  Thr  Ala  Glu  Leu  Ala  Thr  Gln  Ala  Trp  Arg  Gly  Leu  Trp
305                      310                       315                       320

Pro  Thr  Glu  Lys  Ile  Arg  Lys  His  Tyr  Ile  Tyr  Gln  Phe  Gly  Leu  Glu
                    325                       330                       335

Lys  Leu  Met  Arg  Phe  Ser  Glu  Ala  Gln  Leu  Asn  His  His  Phe  Gln  Thr
               340                       345                       350

Phe  Phe  Gly  Leu  Pro  Lys  Glu  Gln  Trp  Tyr  Gly  Phe  Leu  Thr  Asn  Thr
          355                       360                       365

Leu  Ser  Leu  Pro  Glu  Leu  Ile  Gln  Ala  Met  Leu  Arg  Leu  Phe  Ala  Gln
     370                       375                       380

Ala  Pro  Asn  Asp  Val  Arg  Trp  Gly  Leu  Met  Glu  Gln  Gln  Gly  Arg  Glu
385                      390                       395                       400

Leu  Gln  Leu  Phe  Trp  Gln  Ala  Ile  Ala  Ala  Arg
                    405                       410
```

( 2 ) INFORMATION FOR SEQ ID NO:3:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( x i ) SEQUENCE DESCRIPTION: SEQ ID NO:3:

```
Asp  Ala  Leu  Val  Ile  Gly  Ser  Gly  Pro  Ala  Gly  Leu  Ala  Ile  Ala  Ala
1                   5                        10                       15

Glu  Leu  Ala  Gln  Arg  Gly  Leu  Lys  Val  Gln  Gly  Leu  Ser
```

( 2 ) INFORMATION FOR SEQ ID NO:4:

( i ) SEQUENCE CHARACTERISTICS:
      ( A ) LENGTH: 1614 base pairs
      ( B ) TYPE: nucleic acid
      ( C ) STRANDEDNESS: single
      ( D ) TOPOLOGY: linear ( i i ) MOLECULE TYPE: cDNA to mRNA ( v i ) ORIGINAL SOURCE:
      ( A ) ORGANISM: Nicotiana tabacum
      ( B ) STRAIN: cv. xanthii
      ( F ) TISSUE TYPE: Leaf ( x i ) SEQUENCE DESCRIPTION: SEQ ID NO:4:

```
GGAACTTTCT TGAAATCCTG TTTGTAGTTT TCAAAAAAAA TTGAACCCCT GTTGGAAGAT     60
ATGGATACAT TGTTGAAAAC CCCAAATAAG CTTGAGTTTC TGCACCCAGT TCATGGATTT    120
TCTGTTAAAG CTAGCTCCTT TAACTCTGTA AAGCCCCATA AGTTTGGTTC TAGGAAAATT    180
TGTGAAAATT GGGGTAAAGG GGTTTGTGTT AAGGCTAAGA GTAGTGCCCT TTTGGAGCTT    240
GTACCTGAGA CCAAAAAGGA AAATCTTGAT TTTGAGCTTC CTATGTATGA CCCTTCAAAA    300
GGTCTTGTTG TAGATCTAGC TGTGGTTGGT GGTGGACCCG CTGGACTTGC AGTTGCACAG    360
CAGGTTTCGG AGGCTGGACT ATCGGTTGTT TCAATCGATC CATCGCCGAA ATTGATATGG    420
CCCAATAACT ATGGTGTTTG GGTGGATGAA TTTGAGGCCA TGGATTTGTT GGATTGCCTC    480
GACGCCACAT GGTCAGGTAC TGTTGTTTAT ATTGATGACA ATACAACTAA AGATCTTGAT    540
AGACCTTATG GAAGGGTTAA TCGGAAACAA CTTAAGTCCA AAATGATGCA GAAATGCATA    600
CTAAACGGTG TTAAATTCCA CCACGCCAAA GTTATAAAGG TAATTCACGA GGAAGCTAAA    660
TCTATGCTGA TTTGCAATGA TGGTGTAACT ATTCAGGCAA CGGTGGTGCT TGATGCAACT    720
GGCTTCTCAA GATGTCTTGT TCAGTATGAT AAGCCATATA AACCTGGATA TCAAGTAGCT    780
TATGGCATAT TGGCAGAAGT GGAGGAACAT CCCTTTGATA CAAGTAAGAT GGTTCTCATG    840
GATTGGCGAG ATTCGCATCT TGGTAATAAT ATGGAGCTGA AGGAGAGAAA TAGAAAAGTT    900
CCAACTTTTT TGTATGCCAT GCCATTTTCA TCAAATAAAA TATTTCTTGA AGAAACCTCA    960
CTTGTTGCTC GTCCTGGATT ACGTATGGAC GATATTCAAG AAAGAATGGT GGCTCGTTTA   1020
AATCACTTGG GTATAAAAGT TAAGAGCATT GAAGAGGACG AGCATTGTGT AATTCCGATG   1080
GGAGGCTCCC TTCCTGTAAT ACCTCAGAGA GTTGTTGGAA CTGGTGGTAC AGCTGGTCTG   1140
GTTCATCCCT CAACAGGTTA TATGGTAGCA AGGACCCTAG CTGCAGCTCC GGTCGTCGCT   1200
AATGCAATAA TTCACTACCT TGGTTCTGAG AAAGACCTTT TAGGTAATGA GTTATCTGCA   1260
GCTGTTTGGA AAGATTTGTG GCCCATAGAA AGGAGACGTC AACGAGAGTT CTTTTGTTTC   1320
GGTATGGATA TTCTTCTGAA GCTTGATTTA CCCGCTACAA GAAGGTTTTT CGATGCCTTT   1380
TTTGATCTAG AACCTCGTTA TTGGCATGGC TTCTTGTCAT CTCGCCTGTA TCTTCCTGAG   1440
CTTATATTTT TCGGGCTGTC CCTTTTCTCT CGCGCTTCAA ATACTTCTAG AATAGAGATT   1500
ATGACAAAGG GAACTCTTCC TTTGGTAAAT ATGATCAACA ATTTGTTACA GGATACAGAA   1560
TGACTTACCA GGAATCTTGT TCAATATTAC ATAGCATGTG TTAATACACT GCTC         1614
```

( 2 ) INFORMATION FOR SEQ ID NO:5:

( i ) SEQUENCE CHARACTERISTICS:
      ( A ) LENGTH: 1650 base pairs
      ( B ) TYPE: nucleic acid ( C ) STRANDEDNESS: single
( D ) TOPOLOGY: linear ( i i ) MOLECULE TYPE: cDNA to mRNA ( v i ) ORIGINAL SOURCE:
( A ) ORGANISM: Lycopersicon esculentum
( B ) STRAIN: cv. VF36
( F ) TISSUE TYPE: Leaf ( x i ) SEQUENCE DESCRIPTION: SEQ ID NO:5:

```
GGCACGAGGA  AACTTTTCTC  TCTTCACTAG  CTGTTTACAT  GCTTGAAATT  TCAAGATTTT    60
AGGACCCCAT  TTGAAGTTTT  CTTGAAACAA  ATATTACCCT  GTTGGAAAAA  GATGGATACT   120
TTGTTGAAAA  CCCCAAATAA  CCTTGAATTT  CTGAACCCAC  ATCATGGTTT  TGCTGTTAAA   180
GCTAGTACCT  TTAGATCTGA  GAAGCATCAT  AATTTTGGTT  CTAGGAAGTT  TTGTGAAACT   240
TTGGGTAGAA  GTGTTTGTGT  TAAGGGTAGT  AGTAGTGCTC  TTTTAGAGCT  TGTACCTGAG   300
ACCAAAAAGG  AGAATCTTGA  TTTTGAGCTT  CCTATCTATG  ACCCTTCAAA  AGGGGTTGTT   360
GTGGATCTTG  CTGTGGTTGG  TGGTGGCCCT  GCAGGACTTG  CTGTTGCACA  GCAAGTTTCT   420
GAAGCAGGAC  TCTCTGTTTG  TTCAATTGAT  CCGAATCCTA  AATTGATATG  GCCTAATAAC   480
TATGGTGTTT  GGGTGGATGA  ATTTGAGGCT  ATGGACTTGT  TAGATTGTCT  AGATGCTACC   540
TGGTCTGGTG  CAGCAGTGTA  CATTGATGAT  AATACGGCTA  AAGATCTTCA  TAGACCTTAT   600
GGAAGGGTTA  ACCGGAAACA  GCTGAAATCG  AAAATGATGC  AGAAATGTAT  AATGAATGGT   660
GTTAAATTCC  ACCAAGCCAA  AGTTATAAAG  GTGATTCATG  AGGAATCGAA  ATCCATGTTG   720
ATATGCAATG  ATGGTATTAC  TATTCAGGCA  ACGGTGGTGC  TCGATGCAAC  TGGCTTCTCT   780
AGATCTCTTG  TTCAGTATGA  TAAGCCTTAT  AACCCCGGGT  ATCAAGTTGC  TTATGGCATT   840
TTGGCTGAAG  TGGAAGAGCA  CCCCTTTGAT  GTAAACAAGA  TGGTTTTCAT  GGATTGGCGA   900
GATTCTCATT  TGAAGAACAA  TACTGATCTC  AAGGAGAGAA  ATAGTAGAAT  ACCAACTTTT   960
CTTTATGCAA  TGCCATTTTC  ATCCAACAGG  ATATTTCTTG  AAGAAACATC  ACTCGTAGCT  1020
CGTCCTGGCT  TGCGTATAGA  TGATATTCAA  GAACGAATGG  TGGCTCGTTT  AAACCATTTG  1080
GGGATAAAAG  TGAAGAGCAT  TGAAGAAGAT  GAACATTGTC  TAATACCAAT  GGGTGGTCCA  1140
CTTCCAGTAT  TACCTCAGAG  AGTCGTTGGA  ATCGGTGGTA  CAGCTGGCAT  GGTTCATCCA  1200
TCCACCGGTT  ATATGGTGGC  AAGGACACTA  GCTGCGGCTC  CTGTTGTTGC  CAATGCCATA  1260
ATTCAATACC  TCGGTTCTGA  AAGAAGTCAT  TCGGGTAATG  AATTATCCAC  AGCTGTTTGG  1320
AAAGATTTGT  GGCCTATAGA  GAGGAGACGT  CAAAGAGAGT  TCTTCTGCTT  CGGTATGGAT  1380
ATTCTTCTGA  AGCTTGATTT  ACCTGCTACA  AGAAGGTTCT  TTGATGCATT  CTTTGACTTA  1440
GAACCTCGTT  ATTGGCATGG  CTTCTTATCG  TCTCGATTGT  TTCTACCTGA  ACTCATAGTT  1500
TTTGGGCTGT  CTCTATTCTC  TCATGCTTCA  AATACTTCTA  GATTGAGAT  AATGACAAAG  1560
GGAACTGTTC  CATTAGTAAA  TATGATCAAC  AATTTGTTAC  AGGATAAAGA  ATGAATCCGA  1620
GTAATTCGGA  ATCTTGTCCA  ATCTCGTGCC                                      1650
```